US010202578B2

(12) United States Patent
Fife et al.

(10) Patent No.: US 10,202,578 B2
(45) Date of Patent: Feb. 12, 2019

(54) CHICKEN CELLS FOR IMPROVED VIRUS PRODUCTION

(71) Applicant: THE PIRBRIGHT INSTITUTE, Woking, Surrey (GB)

(72) Inventors: Mark Fife, Woking (GB); Mark Gibson, Woking (GB)

(73) Assignee: THE PIRBRIGHT INSTITUTE, Woking, Surrey (GB)

( * ) Notice: Subject to any disclaimer, the term of this patent is extended or adjusted under 35 U.S.C. 154(b) by 0 days.

(21) Appl. No.: 14/895,866

(22) PCT Filed: Jun. 3, 2014

(86) PCT No.: PCT/GB2014/051693
§ 371 (c)(1),
(2) Date: Dec. 3, 2015

(87) PCT Pub. No.: WO2014/195692
PCT Pub. Date: Dec. 11, 2014

(65) Prior Publication Data
US 2016/0108359 A1 Apr. 21, 2016

(30) Foreign Application Priority Data
Jun. 5, 2013 (GB) .................................. 1310031.8

(51) Int. Cl.

| | |
|---|---|
| ***C12N 5/00*** | (2006.01) |
| ***C12N 5/02*** | (2006.01) |
| ***A01K 67/027*** | (2006.01) |
| ***C12N 5/073*** | (2010.01) |
| ***C12N 7/00*** | (2006.01) |
| ***A61K 38/17*** | (2006.01) |
| ***A61K 48/00*** | (2006.01) |
| ***C07K 14/705*** | (2006.01) |
| ***C12Q 1/6876*** | (2018.01) |

(52) U.S. Cl.
CPC .......... *C12N 5/0603* (2013.01); *A61K 38/177* (2013.01); *A61K 48/0066* (2013.01); *C07K 14/70596* (2013.01); *C12N 7/00* (2013.01); *C12Q 1/6876* (2013.01); *C12N 2510/00* (2013.01); *C12N 2740/16051* (2013.01); *C12N 2810/6072* (2013.01); *C12Q 2600/158* (2013.01)

(58) Field of Classification Search
USPC ............................................ 435/325; 800/19
See application file for complete search history.

(56) References Cited

U.S. PATENT DOCUMENTS

2010/0138946 A1 6/2010 Van de Lavoir et al.
2012/0073005 A1* 3/2012 Watanabe .......... A01K 67/0275 800/19

FOREIGN PATENT DOCUMENTS

JP 2001-527422 A 12/2001
JP 2012-526532 A 11/2012
WO WO-99/47645 A1 9/1999
WO WO 2011/072247 * 6/2011
WO WO-2011/072247 A2 6/2011
WO WO-2012/158985 A2 11/2012

OTHER PUBLICATIONS

Everitt (Nature, 2012, vol. 484, No. 7395, p. 519-523).*
Smith (J. Virol., Dec. 2013, vol. 87, No. 23, p. 12957-12966).*
Love et al, (1994) Biotechnology 12:60-63.*
McGrew et al, (2004) EMBO Rep 5:728-733.*
Mozdziak et al, (2003) Dev Dyn 226:439-445 (transgenic chickens.*
Kamihira et al, (2005) J Virol 79: 10864-10874.*
Lillico et al, (2007) Proc Natl Acad Sci USA 104: 1771-1776.*
Written opinion for PCT/G2014/051693, dated May 12, 2015.*
Hernandez (Curr Protoc Microbiology, May 2010, Appendix 4, (A.4I.1-A.4I.8)).*
Schusser (PNAS, Dec. 10, 2013, vol. 110, No. 50, p. 20170-20175).*
Wade (Poultry Sci. 2014, vol. 93, p. 799-809).*
Woolcock (2008, "Avian Influenza Virus Isolation and Propagation in Chicken Eggs". In: Spackman E. (eds) Avian Influenza Virus. Methods in Molecular Biology™, vol. 436. Humana Press).*
Altschul et al., Basic local alignment search tool, *J. Mol. Biol.* 215: 403-10 (1990).
Ausubel et al., Short Protocols in Molecular Biology, 4th Edition, Chapter 18 (1999).
Devereux et al., A comprehensive set of sequence analysis programs for the VAX, *Nucl. Acid Res.* 12: 387-95 (1984).
Everitt, et al., "IFITM3 restricts the morbidity and mortality associated with influenze," Nature 26, vol. 484, No. 7395, pp. 519-523 (Apr. 26, 2012).
NCBI Reference Sequence Accession No. XP-003206160.1, Predicted: interferon-induced transmembrane protein 5-like [Meleagris gallopavo], dated Mar. 25, 2011.
Smith et al., Chicken interferon-inducible transmembrane protein 3 restricts influenza viruses and lyssaviruses in vitro. *J. Virol.* 87(23): 12957-66 (2013).
International Search Report issued in related PCT/GB2014/051693 dated Oct. 17, 2014.
International Preliminary Report on Patentability issued in related PCT/GB2014/051693.

(Continued)

*Primary Examiner* — Michael C Wilson
(74) *Attorney, Agent, or Firm* — Marshall, Gerstein & Borun LLP

(57) ABSTRACT

The present Invention provides as avian cell in which the expression or activity of one or more of the following genes, or a homologue thereof: Chicken IFITM 1 (SEQ ID No. 1); Chicken IFITM2 (SEQ ID No. 2) and Chicken IFITM3 (SEQ ID No. 3) is reduced. The invention also provides methods for passaging viruses in avian cells, embryos and/or avian cell lines which have reduced expression of one or more IFITM genes and methods which involve investigating the sequence of one or more of the following genes, or a homologue thereof: Chicken IFITM1 (SEQ ID No. 1); Chicken IFITM2 (SEQ ID No. 2) and Chicken IFITM3 (SEQ ID No. 3).

8 Claims, 7 Drawing Sheets

Specification includes a Sequence Listing.

(56) References Cited

OTHER PUBLICATIONS

Bailey et al., IFITM-Family Proteins: The Cell's First Line of Defense, *Ann. Rev. Virol.* 1: 261-83 (2014).
Yount et al., Palmitoylome profiling reveals S-palmitoylation-dependent antiviral activity of IFITM3. *Nat. Chem. Biol.* 6(8): 610-4 (2010).
Das et al., A robust system for RNA interference in the chicken using a modified microRNA operon, Dev. Biol., 294(2):554-63 (2006).
Leighton et al., Genetic modification of primordial germ cells by gene trapping, gene targeting, and phiC31 integrase, Mol. Reprod. Dev., 75(7):1163-75 (2008).
Macdonald et al., Efficient genetic modification and germ-line transmission of primordial germ cells using piggyBac and Tol2 transposons, Proc. Natl. Acad. Sci. USA, 109(23):E1466-72 (2012).
Scott et al., Applications of avian transgenesis, ILAR J., 51(4):353-61 (2010).

* cited by examiner

SEQUENCE LISTING

```
<160> NUMBER OF SEQ ID NOS: 22

<210> SEQ ID NO 1
<211> LENGTH: 113
<212> TYPE: PRT
<213> ORGANISM: Gallus gallus

<400> SEQUENCE: 1

Met Gln Ser Tyr Pro Gln His Thr Ser Ile Asn Met Pro Ser Tyr Gly
```

-continued

```
1               5                   10                  15

Gln Asp Val Thr Thr Thr Ile Pro Ile Ser Pro Gln Pro Pro Pro Lys
            20                  25                  30

Asp Phe Val Leu Trp Ser Leu Phe Asn Phe Val Leu Cys Asn Ala Phe
        35                  40                  45

Cys Leu Gly Leu Cys Ala Leu Ser Tyr Ser Ile Lys Ser Arg Asp Arg
    50                  55                  60

Ile Ile Ala Lys Asp Phe Val Gly Ala Ser Ser Tyr Gly Arg Thr Ala
65                  70                  75                  80

Lys Ile Phe Asn Ile Phe Ala Phe Cys Val Gly Leu Leu Val Thr Ile
                85                  90                  95

Leu Ser Ile Val Leu Val Phe Leu Tyr Leu Pro Leu Tyr Thr Val Arg
            100                 105                 110

Pro


<210> SEQ ID NO 2
<211> LENGTH: 113
<212> TYPE: PRT
<213> ORGANISM: Gallus gallus

<400> SEQUENCE: 2

Met Lys Pro Gln Gln Ala Glu Val Ser Ile Pro Leu His Pro Pro Gly
1               5                   10                  15

Arg Gly Pro Pro Leu Ala Ser Leu Pro Asp Glu Gln Pro Arg Asp Phe
            20                  25                  30

Ile Leu Trp Ser Leu Phe Asn Val Leu Ala Gly Phe Ala Leu Ala Tyr
        35                  40                  45

Leu Gly Cys Phe Cys Phe Pro Ser Leu Ile Phe Ser Ile Lys Ala Arg
    50                  55                  60

Asp Cys Lys Val Leu Gly Asp Leu Glu Gly Ala Arg Arg Tyr Gly Ser
65                  70                  75                  80

Arg Ala Lys Val Leu Asn Ile Ile Phe Ser Val Leu Ile Ala Val Gly
                85                  90                  95

Val Leu Ser Thr Ile Thr Ile Ala Ile Met Phe Ile Thr Ala Ile Ser
            100                 105                 110

Arg


<210> SEQ ID NO 3
<211> LENGTH: 137
<212> TYPE: PRT
<213> ORGANISM: Gallus gallus

<400> SEQUENCE: 3

Met Glu Arg Val Arg Ala Ser Gly Pro Gly Val Pro Pro Tyr Glu Pro
1               5                   10                  15

Leu Met Asp Gly Met Asp Met Glu Gly Lys Thr Arg Ser Thr Val Val
            20                  25                  30

Thr Val Glu Thr Pro Leu Val Pro Pro Pro Arg Asp His Leu Ala Trp
        35                  40                  45

Ser Leu Cys Thr Thr Leu Tyr Ala Asn Val Cys Cys Leu Gly Phe Leu
    50                  55                  60

Ala Leu Val Phe Ser Val Lys Ser Arg Asp Arg Lys Val Leu Gly Asp
65                  70                  75                  80

Tyr Ser Gly Ala Leu Ser Tyr Gly Ser Thr Ala Lys Tyr Leu Asn Ile
                85                  90                  95
```

-continued

Thr Ala His Leu Ile Asn Val Phe Leu Ile Ile Leu Ile Ile Ala Leu
100 105 110

Val Ala Ser Gly Thr Ile Met Val Ala Asn Ile Phe Asn His Gln Gln
115 120 125

Gln His Pro Glu Phe Ile Gly Pro Thr
130 135

<210> SEQ ID NO 4
<211> LENGTH: 501
<212> TYPE: DNA
<213> ORGANISM: Gallus gallus

<400> SEQUENCE: 4
acagctgccc tccagcacca tgcagagcta ccctcagcac accagcatca acatgccttc 60
ctacgggcag gatgtgacca ccactattcc catctctccg cagccgcccc ccaaggattt 120
tgtactctgg tccctcttca actttgtgct gtgcaacgcc ttctgcctgg gcttatgtgc 180
tctctcatac tccatcaagt ccagggatag gatcatcgcc aaggacttcg taggcgccag 240
cagctatggg aggacagcga agatctttaa catctttgca ttctgtgtgg gacttcttgt 300
gaccatcctc tccatcgtcc tggtgtttct ctacctcccg ttgtacactg tgcggccctg 360
atctggcctg atcaagagga gcagcactgc ggtcccactc ctccttccct ctacctctgg 420
tatcaccccc accgaggtga ctcagttcgg gatgagccct tggggtgagc tgaaggcaaa 480
taaagcttct tccccattct a 501

<210> SEQ ID NO 5
<211> LENGTH: 342
<212> TYPE: DNA
<213> ORGANISM: Gallus gallus

<400> SEQUENCE: 5
atgaagccgc aacaggcgga ggtgagcatc ccgctgcacc cacccgggcg ggggccgccc 60
ctcgccagcc tccccgacga gcagccccgc gacttcatcc tctggtccct cttcaacgtc 120
ctggcgggct tcgctctcgc ctacctcggc tgcttctgct tcccctcgct catcttctcc 180
atcaaggccc gcgactgcaa agtgctgggc gacctggaag gtgctcggcg gtatggaagc 240
cgggccaagg tgctgaacat catcttctct gtgctgatag ccgtcggtgt gttgtccacc 300
atcaccattg ccatcatgtt catcaccgcg atcagcagat ag 342

<210> SEQ ID NO 6
<211> LENGTH: 749
<212> TYPE: DNA
<213> ORGANISM: Gallus gallus

<400> SEQUENCE: 6
caccgggctg cggggaaacg aaaccagttc cctccgtcct cccgtcccgg cgccgccccc 60
aagcctcata gcccccgagc cccgggatgg agcgggtacg cgcttcgggt ccgggagtcc 120
caccgtatga acccctgatg gacgggatgg acatggaggg gaagacccgc agcacggtgg 180
tgacggtgga gacgcccctg gtgcctcctc cccgcgacca cctggcctgg tcgctgtgca 240
ccacgctgta cgccaacgtc tgctgcctcg gcttcctggc gctcgtcttc tccgtgaagt 300
ccagggatcg caaagtcctg ggtgactaca gcggggcgct cagctatggc tccactgcga 360
agtacctgaa catcacggcc catctgatca acgtcttcct catcatcctc atcatcgccc 420
tggttgccag tggcaccatc atggtggcca acatcttcaa ccaccagcag caacaccccg 480

-continued aattcattgg acccacttag ctccattcca tgggcagagc ttcgcttggg gccatgcttt 540
ccttgcttct tccaatcccc tctccggtca gcatatggaa aagcacctca agacacccct 600
tgctctggca ggaacccgaa aaactggctg tagtgcagac tttgctgctt gccacctcac 660
tctgcctttc tgctattgct ccaagtgccc tgagggcagc acctcattgg taaaaaacac 720
aataaaggta tctttcactt ttgtcccac 749

<210> SEQ ID NO 7
<211> LENGTH: 682
<212> TYPE: DNA
<213> ORGANISM: Gallus gallus

<400> SEQUENCE: 7
ggaccccccg agccccggga tggagcgggt acgcgcttcg ggtccgggag tcccaccgta 60
tgaacccctg atggacggga tggacatgga ggggaagacc cgcagcacgg tggtgacggt 120
ggagacgccc ctggtgcctc ctccccgcga ccacctggcc tggtcgctgt gcaccacgct 180
gtacgccaac gtctgctgcc tcggcttcct ggcgctcgtc ttctccgtga agtccaggga 240
tcgcaaagtc ctgggtgact acagcggggc gctcagctat ggctccactg cgaagtacct 300
gaacatcacg gcccatctga tcaacgtctt cctcatcatc ctcatcatcg ccctggttgc 360
cagtggcacc atcatggtgg ccaacatctt caaccaccag cagcaacacc ccgaattcat 420
tggacccact tagctccatt ccatgggcag agcttcgctt ggggccatgc tttccttgct 480
tcttccaatc ccctctccgg tcagcatatg gaaaagcacc tcaagacacc ccttgctctg 540
gcaggaaccc gaaaaactgg ctgtagtgca gactttgctg cttgccacct cactctgcct 600
ttctgctatt gctccaagtg ccctgagggc agcacctcat tggtaaaaaa cacaataaag 660
gtatctttca cttttgtccc ac 682

<210> SEQ ID NO 8
<211> LENGTH: 21
<212> TYPE: DNA
<213> ORGANISM: Artificial Sequence
<220> FEATURE:
<223> OTHER INFORMATION: Primer chIFITM1 F

<400> SEQUENCE: 8
agcacaccag catcaacatg c 21

<210> SEQ ID NO 9
<211> LENGTH: 21
<212> TYPE: DNA
<213> ORGANISM: Artificial Sequence
<220> FEATURE:
<223> OTHER INFORMATION: Primer chIFITM1 R

<400> SEQUENCE: 9
ctacgaagtc cttggcgatg a 21

<210> SEQ ID NO 10
<211> LENGTH: 20
<212> TYPE: DNA
<213> ORGANISM: Artificial Sequence
<220> FEATURE:
<223> OTHER INFORMATION: Primer chIFITM2 F

<400> SEQUENCE: 10
aggtgagcat cccgctgcac 20

-continued

<210> SEQ ID NO 11
<211> LENGTH: 20
<212> TYPE: DNA
<213> ORGANISM: Artificial Sequence
<220> FEATURE:
<223> OTHER INFORMATION: Primer chIFITM2 R

<400> SEQUENCE: 11
accgccgagc accttccagg 20

<210> SEQ ID NO 12
<211> LENGTH: 19
<212> TYPE: DNA
<213> ORGANISM: Artificial Sequence
<220> FEATURE:
<223> OTHER INFORMATION: Primer chIFITM3 F

<400> SEQUENCE: 12
ggagtcccac cgtatgaac 19

<210> SEQ ID NO 13
<211> LENGTH: 19
<212> TYPE: DNA
<213> ORGANISM: Artificial Sequence
<220> FEATURE:
<223> OTHER INFORMATION: Primer chIFITM3 R

<400> SEQUENCE: 13
ggcgtctcca ccgtcacca 19

<210> SEQ ID NO 14
<211> LENGTH: 20
<212> TYPE: DNA
<213> ORGANISM: Artificial Sequence
<220> FEATURE:
<223> OTHER INFORMATION: Primer GAPDH F

<400> SEQUENCE: 14
actgtcaagg ctgagaacgg 20

<210> SEQ ID NO 15
<211> LENGTH: 19
<212> TYPE: DNA
<213> ORGANISM: Artificial Sequence
<220> FEATURE:
<223> OTHER INFORMATION: Primer GAPDH R

<400> SEQUENCE: 15
gctgagggag ctgagatga 19

<210> SEQ ID NO 16
<211> LENGTH: 125
<212> TYPE: PRT
<213> ORGANISM: Homo sapiens

<400> SEQUENCE: 16

```
Met His Lys Glu Glu His Glu Val Ala Val Leu Gly Ala Pro Pro Ser
1               5                   10                  15

Thr Ile Leu Pro Arg Ser Thr Val Ile Asn Ile His Ser Glu Thr Ser
            20                  25                  30

Val Pro Asp His Val Val Trp Ser Leu Phe Asn Thr Leu Phe Leu Asn
        35                  40                  45

Trp Cys Cys Leu Gly Phe Ile Ala Phe Ala Tyr Ser Val Lys Ser Arg
    50                  55                  60
```

```
Asp Arg Lys Met Val Gly Asp Val Thr Gly Ala Gln Ala Tyr Ala Ser
65                  70                  75                  80

Thr Ala Lys Cys Leu Asn Ile Trp Ala Leu Ile Leu Gly Ile Leu Met
                85                  90                  95

Thr Ile Gly Phe Ile Leu Leu Leu Val Phe Gly Ser Val Thr Val Tyr
            100                 105                 110

His Ile Met Leu Gln Ile Ile Gln Glu Lys Arg Gly Tyr
        115                 120                 125


<210> SEQ ID NO 17
<211> LENGTH: 132
<212> TYPE: PRT
<213> ORGANISM: Homo sapiens

<400> SEQUENCE: 17

Met Asn His Ile Val Gln Thr Phe Ser Pro Val Asn Ser Gly Gln Pro
1               5                   10                  15

Pro Asn Tyr Glu Met Leu Lys Glu Glu Gln Glu Val Ala Met Leu Gly
            20                  25                  30

Val Pro His Asn Pro Ala Pro Pro Met Ser Thr Val Ile His Ile Arg
        35                  40                  45

Ser Glu Thr Ser Val Pro Asp His Val Val Trp Ser Leu Phe Asn Thr
    50                  55                  60

Leu Phe Met Asn Thr Cys Cys Leu Gly Phe Ile Ala Phe Ala Tyr Ser
65                  70                  75                  80

Val Lys Ser Arg Asp Arg Lys Met Val Gly Asp Val Thr Gly Ala Gln
                85                  90                  95

Ala Tyr Ala Ser Thr Ala Lys Cys Leu Asn Ile Trp Ala Leu Ile Leu
            100                 105                 110

Gly Ile Phe Met Thr Ile Leu Leu Ile Ile Ile Pro Val Leu Val Val
        115                 120                 125

Gln Ala Gln Arg
    130


<210> SEQ ID NO 18
<211> LENGTH: 133
<212> TYPE: PRT
<213> ORGANISM: Homo sapiens

<400> SEQUENCE: 18

Met Asn His Thr Val Gln Thr Phe Phe Ser Pro Val Asn Ser Gly Gln
1               5                   10                  15

Pro Pro Asn Tyr Glu Met Leu Lys Glu Glu His Glu Val Ala Val Leu
            20                  25                  30

Gly Ala Pro His Asn Pro Ala Pro Pro Thr Ser Thr Val Ile His Ile
        35                  40                  45

Arg Ser Glu Thr Ser Val Pro Asp His Val Val Trp Ser Leu Phe Asn
    50                  55                  60

Thr Leu Phe Met Asn Pro Cys Cys Leu Gly Phe Ile Ala Phe Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
            100                 105                 110

Leu Gly Ile Leu Met Thr Ile Leu Leu Ile Val Ile Pro Val Leu Ile
        115                 120                 125
```

Phe Gln Ala Tyr Gly
130

<210> SEQ ID NO 19
<211> LENGTH: 125
<212> TYPE: PRT
<213> ORGANISM: Pan troglodytes

<400> SEQUENCE: 19

Met His Lys Glu Glu His Glu Val Ala Val Leu Gly Ala Pro Pro Ser
1 5 10 15

Thr Ile Leu Pro Arg Ser Thr Val Ile Asn Ile His Ser Glu Thr Ser
20 25 30

Val Pro Asp His Val Val Trp Ser Leu Phe Asn Thr Leu Phe Leu Asn
35 40 45

Trp Cys Cys Leu Gly Phe Ile Ala Phe Ala Tyr Ser Val Lys Ser Arg
50 55 60

Asp Arg Lys Met Val Gly Asp Val Thr Gly Ala Gln Ala Tyr Ala Ser
65 70 75 80

Thr Ala Lys Cys Leu Asn Ile Trp Ala Leu Ile Leu Gly Ile Leu Met
85 90 95

Thr Ile Gly Phe Ile Leu Leu Leu Val Phe Gly Ser Val Thr Val Tyr
100 105 110

His Ile Met Leu Gln Ile Ile Gln Glu Lys Arg Gly Tyr
115 120 125

<210> SEQ ID NO 20
<211> LENGTH: 132
<212> TYPE: PRT
<213> ORGANISM: Pan troglodytes

<400> SEQUENCE: 20

Met Asn His Ile Val Gln Thr Phe Ser Pro Val Asn Ser Gly Gln Pro
1 5 10 15

Pro Asn Tyr Glu Met Leu Lys Glu Glu Gln Glu Val Ala Met Leu Gly
20 25 30

Ala Pro His Asn Pro Ala Pro Pro Met Ser Thr Val Ile His Ile Arg
35 40 45

Ser Glu Thr Ser Val Pro Asp His Val Val Trp Ser Leu Phe Asn Thr
50 55 60

Leu Phe Met Asn Pro Cys Cys Leu Gly Phe Ile Ala Phe Ala Tyr Ser
65 70 75 80

Val Lys Ser Arg Asp Arg Lys Met Val Gly Asp Val Thr Gly Ala Gln
85 90 95

Ala Tyr Ala Ser Thr Ala Lys Cys Leu Asn Ile Trp Ala Leu Ile Leu
100 105 110

Gly Ile Phe Met Thr Ile Leu Leu Val Ile Ile Pro Val Leu Val Val
115 120 125

Gln Ala Gln Arg
130

<210> SEQ ID NO 21
<211> LENGTH: 133
<212> TYPE: PRT
<213> ORGANISM: Pan troglodytes

<400> SEQUENCE: 21

Met Asn His Thr Val Gln Thr Phe Phe Ser Pro Val Asn Ser Gly Gln

-continued

```
1               5                   10                  15

Pro Pro Asn Tyr Glu Met Leu Lys Glu Glu His Glu Val Ala Val Leu
            20                  25                  30

Gly Ala Pro His Asn Pro Ala Pro Pro Met Ser Thr Val Ile His Ile
        35                  40                  45

Arg Ser Glu Thr Ser Val Pro Asp His Val Val Trp Ser Leu Phe Asn
    50                  55                  60

Thr Leu Phe Met Asn Pro Cys Cys Leu Gly Phe Ile Ala Phe Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
            100                 105                 110

Leu Gly Ile Leu Met Thr Ile Leu Leu Ile Val Ile Pro Val Leu Ile
        115                 120                 125

Phe Gln Ala Tyr Gly
    130


<210> SEQ ID NO 22
<211> LENGTH: 125
<212> TYPE: PRT
<213> ORGANISM: Homo sapiens

<400> SEQUENCE: 22

Met His Lys Glu Glu His Glu Val Ala Val Leu Gly Pro Pro Pro Ser
1               5                   10                  15

Thr Ile Leu Pro Arg Ser Thr Val Ile Asn Ile His Ser Glu Thr Ser
            20                  25                  30

Val Pro Asp His Val Val Trp Ser Leu Phe Asn Thr Leu Phe Leu Asn
        35                  40                  45

Trp Cys Cys Leu Gly Phe Ile Ala Phe Ala Tyr Ser Val Lys Ser Arg
    50                  55                  60

Asp Arg Lys Met Val Gly Asp Val Thr Gly Ala Gln Ala Tyr Ala Ser
65                  70                  75                  80

Thr Ala Lys Cys Leu Asn Ile Trp Ala Leu Ile Leu Gly Ile Leu Met
                85                  90                  95

Thr Ile Gly Phe Ile Leu Leu Leu Val Phe Gly Ser Val Thr Val Tyr
            100                 105                 110

His Ile Met Leu Gln Ile Ile Gln Glu Lys Arg Gly Tyr
        115                 120                 125
```

CHICKEN CELLS FOR IMPROVED VIRUS PRODUCTION

FIELD OF THE INVENTION

The present invention relates to in avian cell in which the expression and/or activity of at least one interferon inducible transmembrane-protein (IFITM) is reduced.

BACKGROUND TO THE INVENTION

The prevention and control of viral Infection and disease represents a continuing challenge for both medical and veterinary medicine. As such methods for reducing the incidence and severity of viral diseases remain at the forefront of medical and biotechnological research.

The most common strategy currently utilised for the control of viral infection and disease is a vaccination approach. Vaccines may comprise inactivated viruses or purified products thereof which have treated with chemicals such as an aziridine, for example binary ethyleneimine (BEI). Alternatively vaccines may comprise live, attenuated viruses that have been cultivated under conditions that lead to a loss of virulence whilst retaining immunogenicity. For example, the disease-causing virus may be passaged through a series of cell cultures or animal embryos until a point at which it is sufficiently poor at replicating in its target cells that it can be used as a vaccine. At this point the virus has lost virulence but is still immunogenic and able to stimulate an immune response.

Embryonated chicken eggs and primary chicken embryonic fibroblasts (CEF) are commonly used for the manufacturing of human and veterinary viral vaccines, including traditional large volume vaccines such as influenza or Newcastle Disease vaccines as well as more modern recombinant viral vectors for vaccines (eg. poxviruses). Embryonated chicken eggs and CEFs are used for passaging viruses in order to generated non-virulent attenuated viruses. Examples of vaccines which utilise attenuated viruses include measles vaccine, mumps vaccine, rubella vaccine, oral polio vaccine (Sabin) and yellow fever vaccine.

The global burden of viral diseases on both animal and human health results in a requirement for the mass production of inactivated and attenuated viruses for use in vaccines. In addition, the outbreak of seasonal pandemics, for example of influenza, requires the production of a large amount of virus in a short-time period. In fact, the global availability of a therapeutically effective influenza virus vaccine during a pandemic remains a major challenge for the biopharmaceutical industry.

A current issue impacting the use of embryonated chicken eggs and CEFs in the production of viruses for vaccines is the time takes to generate the large amount of virus that is required. Further, a draw back to the use of live, attenuated viruses in vaccines is the length of time taken to achieve a sufficient number of passages in a host cell in order to generate an attenuated virus. The highly attenuated modified vaccinia virus Ankara (MVA), for example, which serves as a candidate vaccine to immunize against infectious diseases and cancer, required more than 500 passages in CEFs to generate an attenuated MVA which had lost a substantial part of coding genome sequences and demonstrated a severe restriction of replication on mammalian cells. In addition, restrictions on the passage rate of viruses in host cells may serve as a limiting step influencing virus production and yield.

There is thus a need for methods which increase the yield and efficiency of production of both inactivated and attenuated viruses in systems such as embryonated chicken eggs and CEFs for the production of vaccines.

The IFITM gene cluster on Gga5 is flanked by ATHL1 and B4GALNT4. This region is syntenic with the IFITM gene cluster on Hs11 (A). An alignment of human (SEQ ID NOs: 22 and 17-18), chimp (SEQ ID NOs: 19-21) and chicken (SEQ ID NOs: 1-3) orthologues was carried out using ClustalW and manual alignment refinement and annotated using BioEdit. The boxed columns show residues which are shared between all 9 IFITM sequences. Significant residues have been highlighted with a symbol below the sequence: Δ—Tyrosine; O—double cysteine; *—Phenylalanine important for multimerisation; ↑—conserved ubiquitinated lysine. IM1 (Intramembrane 1), CIL (conserved intracellular loop), IM2 (intramembrane 2).

Figure 2:
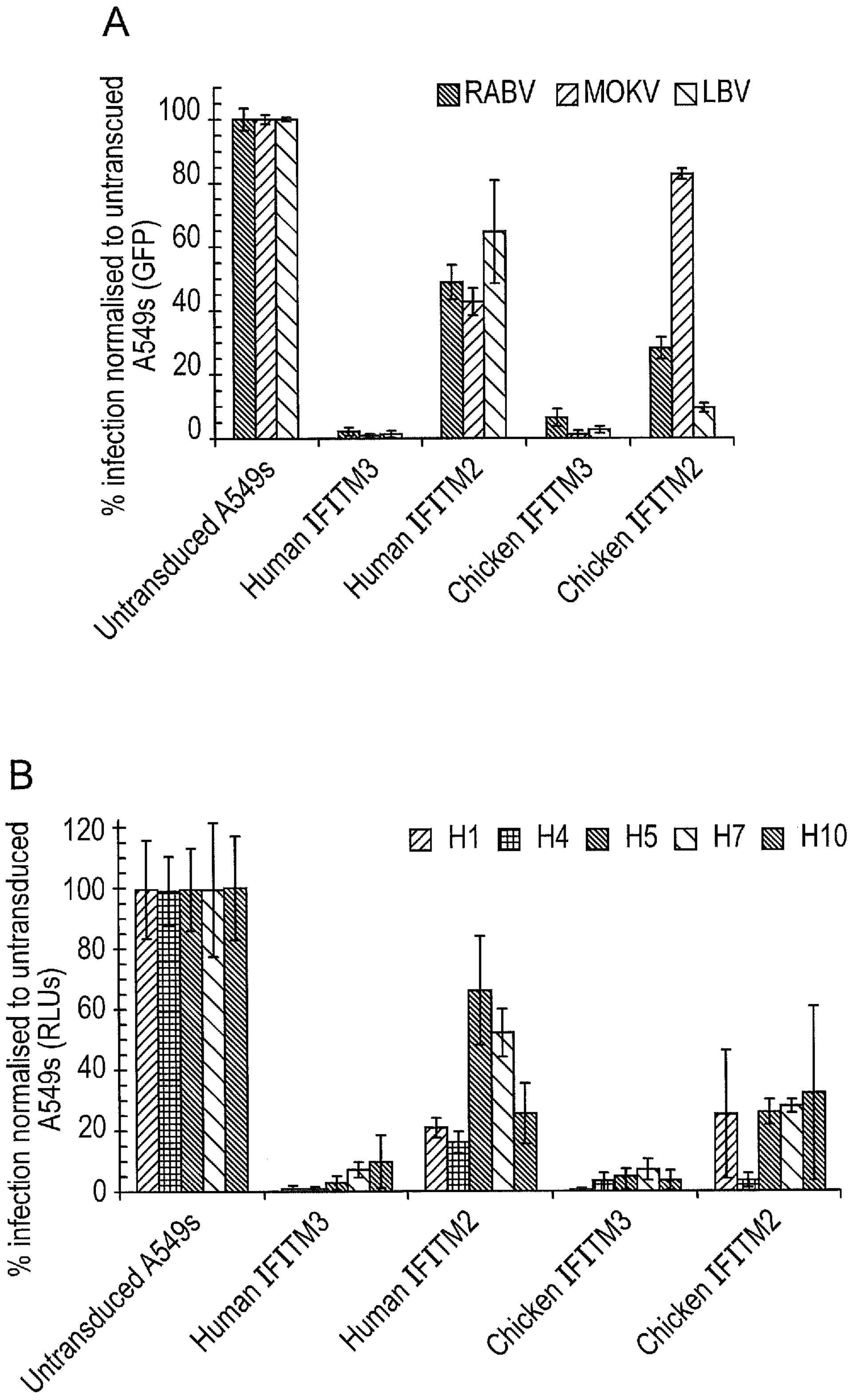

FIG. 2: infection of A549 cells with a range of pseudotyped viruses with either lyssavirus glycoprotein envelopes (CVS; challenge virus standard (Rabies virus), MHK; Mokola virus and RV1; Lagos but virus) or influenza haemagglutinin envelopes (H1 (human), H4 (bird) and H5 (human), H7 (bird), H10 (bird).

Figure 3:
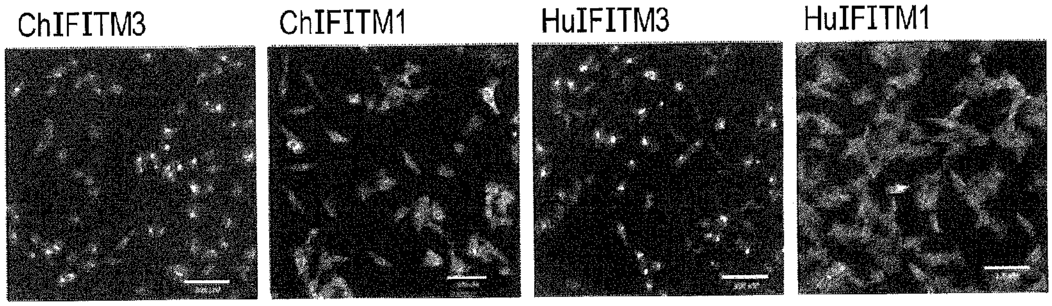

FIG. 3: Cellular localisation of overexpressed IFITM proteins A549 cells.

Figure 4:
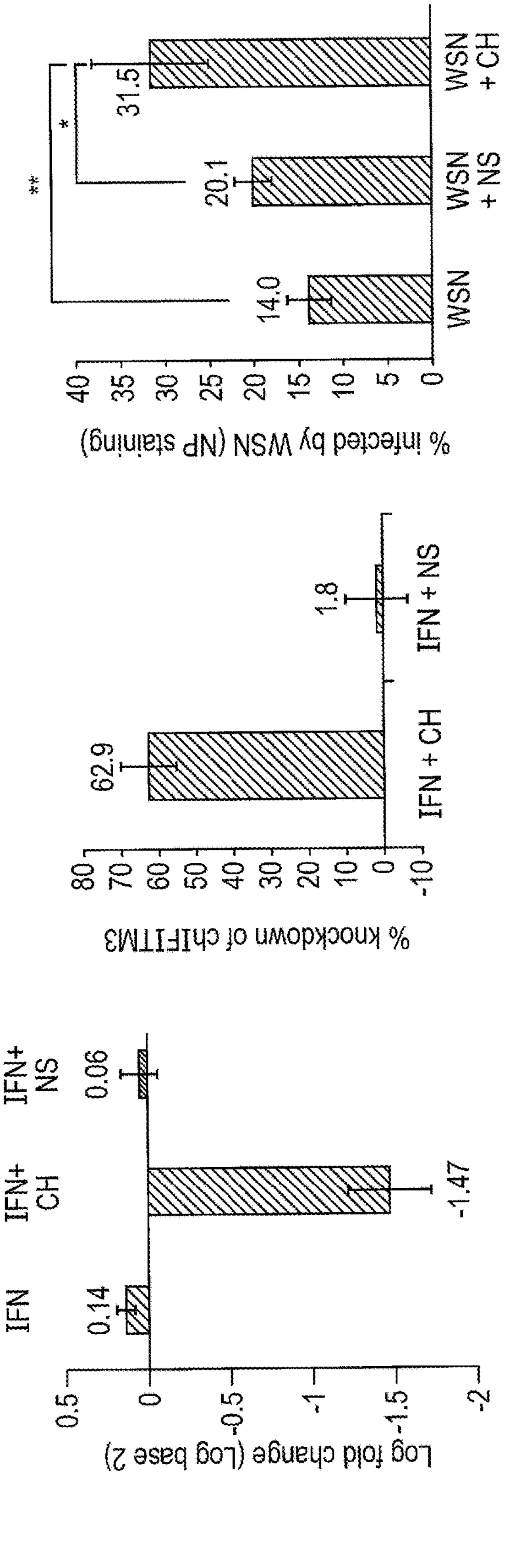

FIG. 4: (A) The log fold change in chIFITM3 expression in DF-1 chicken cells after IFN-γ stimulation, (B) percentage of chIFITM3 knockdown with siRNA specific to chIFITM3 (CH) or a scrambled siRNA (NS), (C) infection of DF-1 cells with influenza A virus (A/WSN/1933 (WSN/33), measured by flow cytometry using an antibody against nucleoprotein (NP). Preincubation with an siRNA specific to chIFITM3 (CH) or a scrambled siRNA (NS) was used in all cases. Error bars represent standard deviation across each condition carried out in triplicate.

Figure 5:
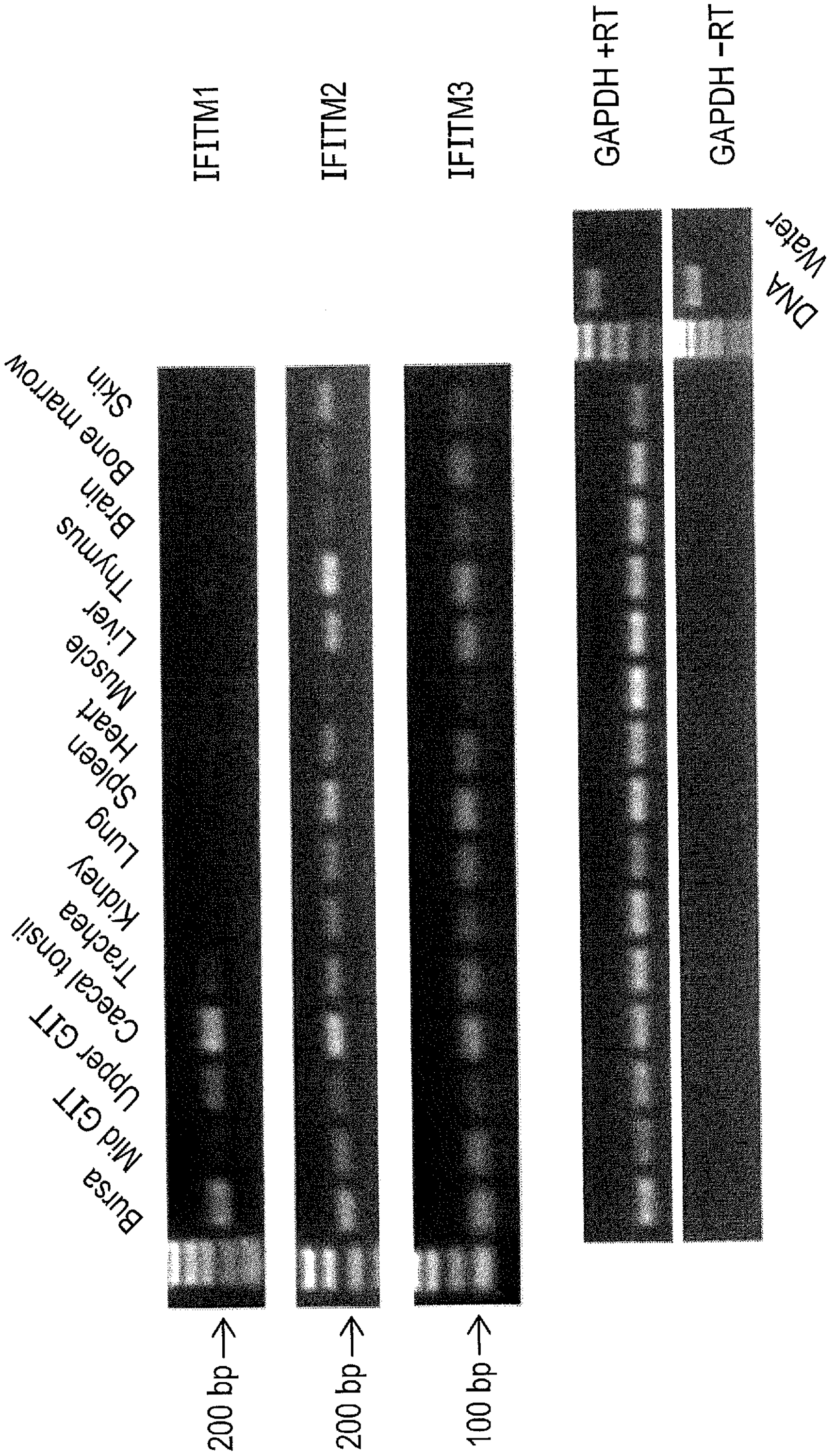

FIG. 5: Differential expression of Chicken IFITM transcripts in a tissue panel.

Figure 6:
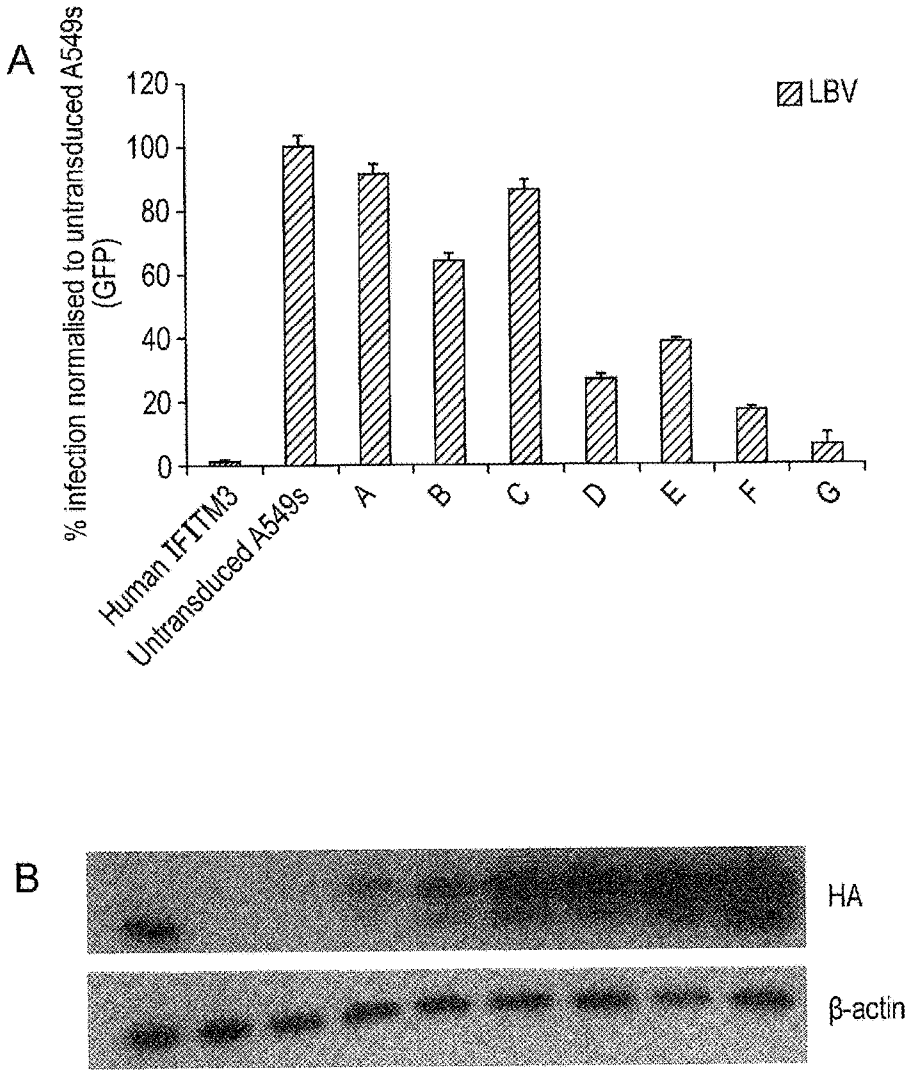

FIG. 6: A549 cells expressing different levels of chIFITM3 protein by western blot of the HA tag (B) restricted the replication of a lentivirus pseudotyped with the Lagos Bat virus (LBV) glycoprotein envelope according to the level of protein expressed (A).

Figure 7:
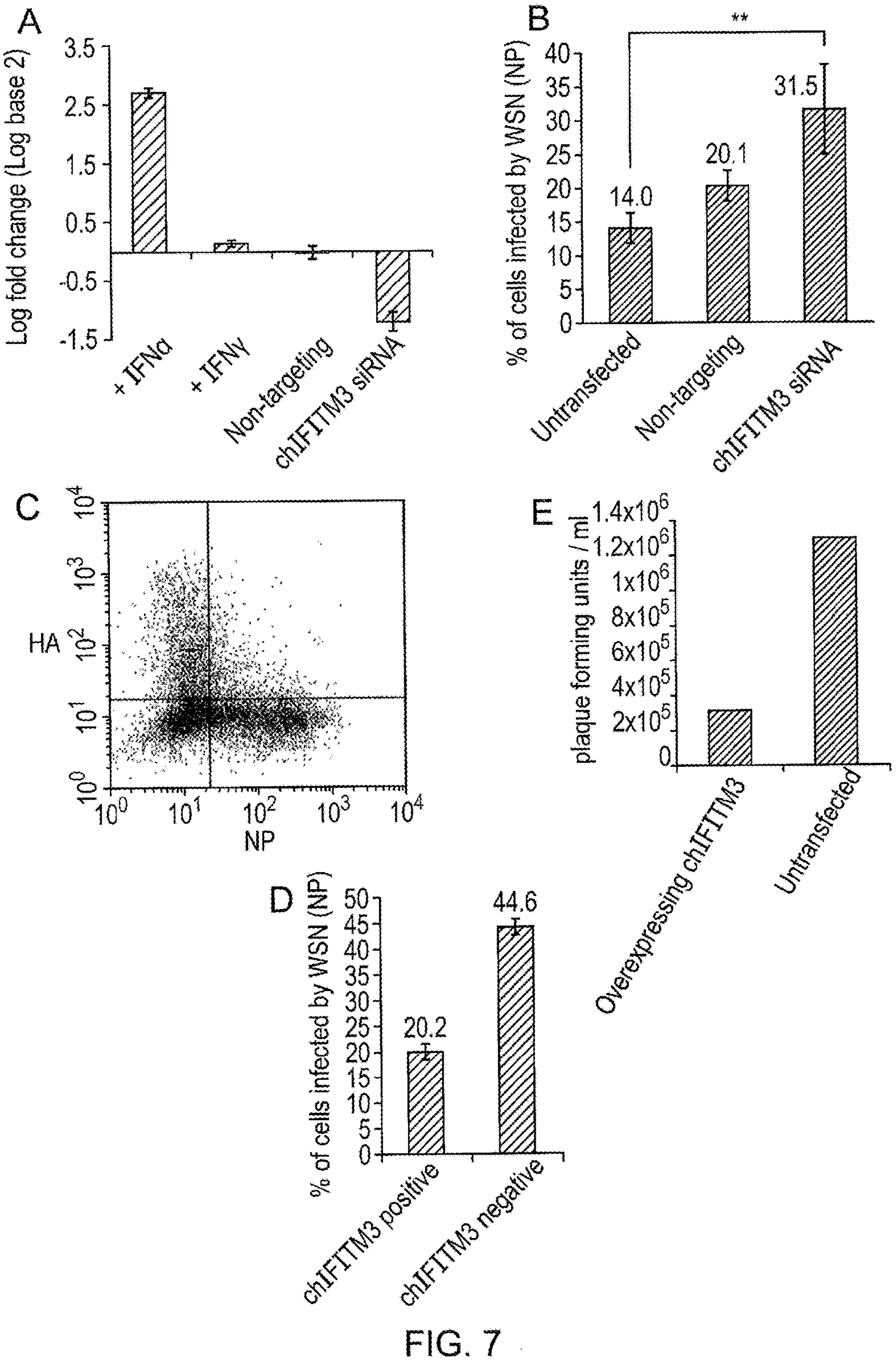

FIG. 7: Chicken IFITM3 has in antiviral activity in DP-1 chicken cells. The expression level and log fold change of chIFITM3 were measured using quantitative RT-PCR after stimulation with IFN-α and IFN-γ or alter preincubation with a nontargeting siRNA or one specific to chIFITM3 (A). The effect of knocking down endogenous chIFITM3 expression in DF-1 cells infected with influenza A virus (A/WSN/1933 [WSN/33]) was measured by flow cytometry using as antibody against nucleoprotein (NP) (B). P=0.01, Student's test. DF-1 cells transfected with chIFITM3-HA were infected by WSN. Expression of HA and NP was detected by flow cytometry (C and D), and viral titers were measured by PFU (E). Error bars represent standard deviations across each condition performed in triplicate.

SUMMARY OF ASPECTS OF THE INVENTION

The interferon-inducible transmembrane (IFITM) protein family is an interferon-stimulated gene family that restricts the replication of several highly pathogenic human viruses, including SARS coronavirus, filoviruses (Marburg virus and Ebola virus), influenza. A viruses and flaviviruses (Dengue virus). Although the IFITM locus, which includes IFITM1, 2, 3 and 5, is present in mammalian species, this locus has not been identified and characterised in avian species. The present inventors have shown that the IFITM locus exists in chickens and identify novel avian IFITM sequences that are associated with an ability to inhibit viral infection of a cell when expressed in that cell.

These identified IFITM sequences may facilitate improved methods of passaging and propagating viruses in avian host cells. They may also be used in methods for screening avian animals for resistance to viral infections and for selecting animals within a population with increased resistance to viral infection.

Thus in a first aspect the present invention provides in avian cell having reduced expression and/or activity of one or more of the following polypeptides or a homologue thereof: Chicken IFITM1 (SEQ ID No. 1); Chicken IFITM2 (SEQ ID No. 2) and Chicken IFITM3 (SEQ ID No. 3).

The cell may have reduced expression of Chicken IFITM3 (SEQ ID No. 3) or a homologue thereof.

The avian cell may be within an avian embryo. The avian cell may be derived from an avian embryo. For example the avian cell may be a chicken embryonic fibroblast cell (CEF).

The cell may be part of an organ, egg, bird or any other animal.

The avian cell may comprise a mutant version of one or more of the following polypeptides, or a homologue thereof: Chicken IFITM1 (SEQ ID No. 1); Chicken IFITM2 (SEQ ID No. 2) and Chicken IFITM3 (SEQ ID No. 3), wherein the mutant version is associated with a decreased resistance to viral infection.

The genome of the avian cell may lack one or more of the nucleotide sequences encoding for one of following polypeptides, or a homologue thereof: Chicken IFITM1 (SEQ ID No. 1); Chicken IFITM2 (SEQ ID No. 2) and Chicken IFITM3 (SEQ ID No. 3).

Alternatively, expression of one or more of the following polypeptides, or a homologue thereof: Chicken IFITM1 (SEQ ID No. 1); Chicken IFITM2 (SEQ ID No. 2) and Chicken IFITM3 (SEQ ID No. 3) may be reduced in the avian cell by RNA interference (RNAi).

In a second aspect, the present invention relates to a method for propagating a virus comprising the following steps:

(i) transducing an avian cell according to the first aspect of the invention with a virus; and;

(ii) passaging the cell in order to propagate the virus.

In a third aspect, the present invention provides a method for producing a vaccine comprising the following steps:

(i) propagating a virus according to the method of second aspect of the invention; and, (ii) incorporating the propagated virus into a vaccine.

In a fourth aspect, the present invention provides a method for generating an attenuated virus comprising the following steps:

(i) transducing an avian cell according to the first aspect of the invention with a virus; and, (ii) passaging the avian cell such that the virus completes multiple rounds of infection and becomes attenuated.

In a fifth aspect, the present invention provides a method for producing a vaccine, comprising the following steps:

(i) attenuating a virus according to fourth aspect of the invention;

(ii) propagating the attenuated virus; and, (iii) incorporating the virus generated in (ii) into a vaccine.

In the method of the fifth aspect of the invention, step (ii) may be performed according to the method of the second aspect of the invention.

In the method according to any of the second to fifth aspects, the virus may enter through acidic endosomes.

In a sixth aspect, the present invention provides a transgenic avian animal in which the expression or activity of one or more of the following polypeptides, or a homologue thereof: Chicken IFITM1 (SEQ ID No. 1); Chicken IFITM2 (SEQ ID No. 2) and Chicken IFITM3 (SEQ ID No. 3) is reduced, knocked-down or knocked-out.

In a seventh aspect, the present invention provides a transgenic avian animal whose germ cells and somatic cells comprise a heterogenic version of one or more nucleotide sequences encoding for one or more of the following polypeptides, or a homologue thereof: Chicken IFITM1 (SEQ ID No. 1); Chicken IFITM2 (SEQ ID No. 2) and Chicken IFITM3 (SEQ ID No. 3) which gene was introduced into said animal, or an ancestor of said animal, at an embryonic stage.

In an eighth aspect, the present invention provides a transgenic avian animal in which the copy number of one or more gene(s) encoding the following polypeptides, or a homologue thereof: Chicken IFITM1 (SEQ ID No. 1); Chicken IFITM2 (SEQ ID No. 2) and Chicken IFITM3 (SEQ. ID No. 3) is increased.

The transgenic animal according to the sixth, seventh or eighth aspects of the invention may be a domestic poultry animal. For example, the transgenic animal may be a chicken.

In an ninth aspect, the present invention provides an avian cell according to first aspect of the invention which is derived from a transgenic avian animal, according to sixth, seventh or eighth aspect of the invention.

In a tenth aspect, the present invention relates to a method for investigating the innate resistance of an avian animal to viral infection which comprises the step of investigating the nucleotide sequence encoding for one or row of the following polypeptides, or a homologue thereof: Chicken IFITM1 (SEQ ID No. 1); Chicken IFITM2 (SEQ ID No. 2) and Chicken IFITM3 (SEQ ID No. 3) and/or investigating the copy number of the nucleotide sequence on the genome.

In a eleventh aspect, the present invention provides a method for selecting an avian animal having resistance to viral infection from a plurality of avian animals of the same species, which comprises the following steps:

(i) investigating the nucleotide sequence encoding for one or more of the following polypeptides, or a homologue thereof in the plurality of avian animals: Chicken IFITM1 (SEQ ID No. 1); Chicken IFITM2 (SEQ ID No. 2) and Chicken IFITM3 (SEQ ID No. 3)) and/or the copy number of the nucleotide sequence on the genome;

(ii) selecting an avian animal having an IFITM1, IFITM2 and/or IFITM3 nucleotide sequence and/or copy number which is associated with resistance to viral infection.

The plurality of avian animals may exhibit genetic and/or copy number variation at the IFITM locus.

The viral infection may be mediated by a virus which enters through acidic endosomes. For example the viral infection may be mediated by avian influenza virus (AIV), Infections Bronchitis Virus (IBV), Infectious Bursal Disease Virus (IBDV) or Newcastle Disease Virus (NDV).

In a twelfth aspect the present invention provides a method for preventing or treating a viral infection in an avian animal which comprises the step of increasing the expression of one or more of the following polypeptides, or a homologue thereof: Chicken IFITM1 (SEQ ID No. 1); Chicken IFITM2 (SEQ ID No. 2) and Chicken IFITM3 (SEQ ID No. 3) in the animal.

In a thirteenth aspect the present invention provides an avian IFITM polypeptide which comprises the amino acid sequence SEQ ID No. 2 (Chicken IFITM2) or variant or homolog thereof.

The avian IFITM polypeptide may comprise one or more, or all of the following amino acid residues: Trp35, Ser36, Leu37, Arg64, Asp65, Asp71, Gly74, Ala75, Tyr78, Ala82, Lys83, Asn86 and Ile87 with reference to the amino acid position numbering given in SEQ ID No. 2.

A variant or homologous avian IFITM polypeptide may comprise an amino acid sequence having at least 80% homology to SEQ ID No. 2.

The avian IFITM polypeptide may, when expressed in a cell, inhibit viral infection of the cell.

In a fourteenth aspect, the present invention provides a nucleic acid sequence encoding a polypeptide according to the twelfth aspect of the invention.

The identification of the avian IFITM locus facilitates the ability to decrease the resistance of avian cells used to passage viruses to viral infection. This decreased resistance of the avian host cells to viral infection increases the infection rate of the virus thereby improving the efficiency of virus passaging in avian host cells. The present invention tints provides methods for passaging viruses in avian cells, for example in order to produce viruses for use in vaccines and to generate attenuated viruses.

In addition, the control of pathogens is a key component of ensuring food security, with both endemic and exotic viruses posing significant threats particularly to the poultry industry and small scale poultry farmers. The identification and characterisation of the avian IFITM locus performed by the present inventors will provide improved methods for combatting important viral diseases of poultry, therefore improving food security.

The identification of the avian IFITM locus will facilitate the selection and breeding of birds with increased resistance to viral infection and enable the generation of transgenic animals expressing exogenous IFITM sequences associated with an increased resistance to viral infections. As such the present invention provides strategies and methodologies to increase the innate viral resistance of poultry flocks and therefore control the introduction and spread of viruses within poultry populations and reduce the present reliance on vaccination programs.

DETAILED DESCRIPTION

IFITMs

The present invention relates to avian IFITM polypeptides.

Interferon-inducible transmembrane (IFITM) proteins restrict the entry processes and replication of several highly pathogenic human viruses, including SARS coronavirus, filoviruses (Marburg, virus and Ebola virus), influenza A (IAV), flaviviruses (Dengue virus) and HIV-1. Their expression is induced by Type I and II interferons and as such they fall within the category of interferon-stimulated genes (ISGs).

IFITM proteins are small (~130aa) and share a common topology defined by a conserved CD225 domain. The CD225 domain comprises two intramembrane (IM) regions (IM1 and IM2) and a conserved intracellular loop (CIL) and is flanked by an N-terminal and a C-terminal domain.

In humans, IFITM1, 2 and 3 are expressed in a wide range of tissues, while IFITM5 expression is limited to osteoblasts. Mice have orthologues for IFITM1, 2, 3 and 5 and additional genes Ifitm6 and Ifitm7.

IFITM proteins inhibit viral infection by blocking cytoplasmic entry and replication of diverse enveloped viruses. IFITM protein-mediated restriction occurs at entry sites of IFITM-restricted viruses in the late endosomal and lysosomal components where the proteins are predicted to adopt an intramembrane structure. IFITM-mediated restriction therefore precedes viral replication, with apparently no opportunity for the synthesis of viral encoded countermeasures.

IFITM proteins prevent the formation of a fusion pore between virus and endosomal membranes following acidic activation of virus envelope fusion proteins. The ability of IFITM proteins to alter cellular membrane properties has been demonstrated, leading to the arrest of fusion pore formation at the stage of hemi-membrane fusion. Depletion of Ifitm3 in mouse cells results in a loss of 40%-70% of IFN-mediated protective effect against endosomal entering virus and a similar attenuation is also detected in the IfitmDel mice, lacking Ifitm1, 2, 3, 5 and 6. Direct clinical evidence for IFITM3 involvement in virus restriction has recently been shown by an association between IFITM3 variants and the number of Individuals hospitalised with seasonal or pandemic influenza H1N1/09 viruses.

The chicken genome contains two putative IFITM genes on chromosome 5, the so-called IFITM5 (ENSGALG00000004239; chromosome 5:1620304-1621805:1) and IFITM10 (ENSGALG00000020497; chromosome 5:15244061-15249351:1). Previous genome analysis of chickens, based on nucleotide sequence homology, has predicted the existence of two additional IFITMs orthologous to human IFITM1 (variant 1: XM_001233949.2; variant 2: XM_003641281.1) and IFITM3 (XM_420925.3). Such genome analysis is often confounded by inappropriate identification of pseudogenes and misalignment of orthologues due to an incomplete knowledge of gene duplication and evolutionary divergence events during speciation. This is especially relevant for the predicted, avian IFITM sequences as their nucleotide sequences differs significantly from the human and chimp orthologues. There have been no previous reports of avian polypeptides providing an IFITM-like function.

The present inventors have performed careful genomic analysis of synthenic regions and functional characterisation of the gene products in order to define functional avian IFITM nucleotide and polypeptide sequences.

The present invention relates to avian IFITM polypeptides which comprises the amino acid sequence selected from the group comprising; SEQ ID No 1 (Chicken IFITM1), SEQ ID No 2 (Chicken IFITM2), SEQ ID No 3 (Chicken IFITM3), and monologues and variants thereof.

```
SEQ ID No 1:
MQSYPQHTSINMPSYGQDVTTTIPISPQPPPKDFVLWSLFNFVLCNAFCL

GLCALSYSIKSRDRIIAKDFVGASSYGRTAKIFNIFAFCVGLLVTILSIV

LVFLYLPLYTVRP

SEQ ID No 2:
MKPQQAEVSIPLHPPGRGPPLASLPDEQPRDFILWSLFNVLAGFALAYLG

CFCFPSLIFSIKARDCKVLGDLEGARRYGSRAKVLNIIFSVLIAVGVLST

ITIAIMFITAISR
```

-continued

SEQ ID No 3:
MERVRASGPGVPPYEPLMDGMEGKTRSTVVTVETPLVPPPRDHLAWSLCT

TLYANVCCLGFLALVFSVKSRDRKVLGDYSGALSYGSTAKYLNITAHLIN

VFLIILIIALVASGTIMVANIFNHQQQHPEFIGPT

The term "polypeptide" is used in the conventional sense to mean a series of residues, typically L-amino acids, connected one to the other, typically by peptide bonds between the α-amino and carboxyl groups of adjacent amino acids.

These chIFITM polypeptides may be encoded by cDNA sequences according to the following sequences; chIFITM1 (SEQ ID No 4), chIFITM2 (SEQ ID No 5), chIFITM3 (SEQ ID No 6 and SEQ ID No 7).

SEQ ID No 4:
acagctgccctccagcaccatgcagagctaccctcagcacaccagcatcaacatgccttc ctacgggcaggatgtgaccaccactattcccatctctccgcagccgcccccaaggattt tgtactctggtccctcttcaactttgtgctgtgcaacgccttctgcctgggcttatgtgc tctctcatactccatcaagtccagggataggatcatcgccaaggacttcgtaggcgccag cagctatgggaggacagcgaagatctttaacatctttgcattctgtgtgggacttcttgt gaccatcctctccatcgtcctggtgtttctctacctcccgttgtacactgtgcggccctg atctggcctgatcaagaggagcagcactgcggtcccactcctccttccctctacctctgg tatcacccccaccgaggtgactcagttcgggatgagcccttggggtgagctgaaggcaaa taaagcttcttccccattcta SEQ ID No 5:
ATGAAGCCGCAACAGGCGGAGGTGAGCATCCCGCTGCACCCACCCGGGCGGGGGCCGCCC

CTCGCCAGCCTCCCCGACGAGCAGCCCCGCGACTTCATCCTCTGGTCCCTCTTCAACGTC

CTGGCGGGCTTCGCTCTCGCCTACCTCGGCTGCTTCTGCTTCCCCTCGCTCATCTTCTCC

ATCAAGGCCCGCGACTGCAAAGTGCTGGGCGACCTGGAAGGTGCTCGGCGGTATGGAAGC

CGGGCCAAGGTGCTGAACATCATCTTCTCTGTGCTGATAGCCGTCGGTGTGTTGTCCACC

ATCACCATTGCCATCATGTTCATCACCGCGATCAGCAGATAG

SEQ ID No 6:
caccgggctgcggggaaacgaaaccagttccctccgtcctcccgtcccggcgccgccccc aagcctcatagcccccgagccccgggatggagcgggtacgcgcttcgggtccgggagtcc caccgtatgaacccctgatggacgggatggacatggaggggaagacccgcagcacggtgg tgacggtggagacgcccctggtgcctcctccccgcgaccacctggcctggtcgctgtgca ccacgctgtacgccaacgtctgctgcctcggcttcctggcgctcgtcttctccgtgaagt ccagggatcgcaaagtcctgggtgactacagcggggcgctcagctatggctccactgcga agtacctgaacatcacggcccatctgatcaacgtcttcctcatcatcctcatcatcgccc tggttgccagtggcaccatcatggtggccaacatcttcaaccaccagcagcaacaccccg aattcattggacccacttagctccattccatgggcagagcttcgcttggggccatgcttt ccttgcttcttccaatcccctctccggtcagcatatggaaaagcacctcaagacacccct tgctctggcaggaacccgaaaaactggctgtagtgcagactttgctgcttgccacctcac tctgcctttctgctattgctccaagtgccctgagggcagcacctcattggtaaaaaacac aataaaggtatctttcacttttgtcccac SEQ ID No 7:
ggacccccgagccccgggatggagcgggtacgcgcttcgggtccgggagtcccaccgta tgaacccctgatggacgggatggacatggaggggaagacccgcagcacggtggtgacggt ggagacgcccctggtgcctcctccccgcgaccacctggcctggtcgctgtgcaccacgct gtacgccaacgtctgctgcctcggcttcctggcgctcgtcttctccgtgaagtccaggga tcgcaaagtcctgggtgactacagcggggcgctcagctatggctccactgcgaagtacct -continued

```
gaacatcacggcccatctgatcaacgtcttcctcatcatcctcatcatcgccctggttgc

cagtggcaccatcatggtggccaacatcttcaaccaccagcagcaacaccccgaattcat

tggacccacttagctccattccatgggcagagcttcgcttggggccatgctttccttgct

tcttccaatcccctctccggtcagcatatggaaaagcacctcaagacaccccttgctctg

gcaggaacccgaaaaactggctgtagtgcagactttgctgcttgccacctcactctgcct

ttctgctattgctccaagtgccctgagggcagcacctcattggtaaaaaacacaataaag

gtatctttcacttttgtcccac
```

The present inventors have determined that the avian IFITM polypeptides are capable of restricting infection by a diverse range of viruses.

The chIFITM polypeptides are able to restrict infection of a host cell by human viruses that do not commonly target avian cells. The chIFITM sequences may therefore be useful in manipulating the susceptibility of host cells to a wide-range of viruses, including viruses that do not commonly target a cell type of that species.

The term "avian" is used in the conventional sense to refer to an animal within the phylogenetic class of Aves.

Specifically, the term avian may relate to animals within the Galliformes family, which includes, but is not limited to, chicken, turkey, grouse, quail, partridge and pheasant.

The avian animal may be a domestic poultry animal, for example a chicken or a turkey.

Homologues and Variants

The term "homologue" refers to a polypeptide from soother avian animal that has an equivalent function to the amino acid sequence selected from the group of SEQ ID No 1, SEQ ID No 2 and SEQ ID No 3. The avian IFITM homologue may be from a related species (i.e. another avian animal from the Galliformes family) or from a different strain of the same species (e.g. another strain of chicken).

The term "variant" refers to a polypeptide that has an equivalent function to the amino acid sequence selected from the group of SEQ ID No 1, SEQ ID No 2 and SEQ ID No 3, but which includes one or more amino acid substitutions, insertions or deletions. A variant IFITM polypeptide may be made by methods known is the art such as site-directed mutagenesis or error-prone PCR.

Functional equivalence relates to the ability of the IFITM polypeptide to inhibit the viral infection of a cell when expressed in that cell.

The avian IFITM homologue may independently fold to form a structure comprising a CD225 domain.

The avian IFITM polypeptide may comprise one or more, or all of the following amino acid residues; Trp35, Ser36, Leu37, Arg64, Asp65, Asp71, Gly74, Ala75, Tyr78, Ala82, Lys83, Asn86 and Ile87 with reference to the amino acid position numbering given in SEQ ID No. 2.

A variant or homologous avian IFITM polypeptide may comprise an amino acid sequence having at least 70, 80, 90, 95 or 98% homology to SEQ ID No. 1, 2 or 3.

Identity comparisons can be conducted by eye, or more usually, with the aid of readily available sequence comparison programs. These commercially available computer programs can calculate % identity between two or more sequences, A suitable computer program for carrying out such an alignment is the GCG Wisconsin Bestfit package (University of Wisconsin, U.S.A.; Devereux et al., 1984, Nucleotide sequences Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching.

Once the software has produced ah optimal alignment, it is possible to calculate % identity. The software typically does this as part of the sequence comparison and generates a numerical result.

Due to the redundancy of the genetic code, variations in the sequences of SEQ ID No 4-7 are possible that encode for the same polypeptide. These sequences are encompassed by the present invention.

Single nucleotide polymorphisms (SNPs), insertions and deletions in the encoding nucleotide sequence and other variation within avian IFITM polypeptides may impact the anti-viral function of the polypeptide. IFITM variants may therefore be active or inactive variants, wherein an active variant is an IFITM polypeptide with an anti-viral activity that is equal to or greater than the wild-type sequence and an inactive variant is an IFITM polypeptide with an anti-viral activity less than the wild-type sequence. Variant IFITM sequences may be referred to as mutant sequences.

A wild-type protein refers to a protein comprising a sequence of amino acids that is the non-mutated version of an amino acid sequence that is common in the general population.

IFITM sequence variants may exist within a flock, a breed and/or a species of avian animals. These IFITM sequence variants may be active or inactive variants, associated with different levels of resistance to viral infection, and as such individual animals within the flock, breed and/or species may be associated with different levels of resistance to viral infection.

Propagating and Attenuating Viruses

The present invention provides methods for propagating viruses by transducing an avian cell with a virus and passaging the cell in order to propagate the virus.

The avian cell may form part of an avian embryo, it may be derived from an avian embryo or it may be an avian cell line.

The cell may be any avian cell or avian cell line.

Viruses for use in vaccines are commonly produced via propagation in embryonated chicken eggs and/or cells derived from embryonated chicken eggs, for example chicken embryonic fibroblasts (CEFs).

General techniques for the propagation of viruses in avian cells are well known in the art.

The term "transduce" is used in its conventional sense to refer to the transduction of genetic material into a host cell via a viral vector. In the present case this refers to the transduction of the viral genetic material into the host cell such that the virus can replicate in order that virus progeny generated are released from the host cell to infect other cells.

The term “propagate” refers to increasing the number or amount of virus particles.

The phase “passaging the cell” refers to facilitating or enabling the division and/or maintenance of the avian host cell such that virus infects multiple cells within the population, enabling viral replication and propagation to occur.

If the avian cell forms part of art avian embryo, for example if it is an embryonated chicken egg, passaging the cell may refer to providing the appropriate environment such that the virus is able to infect a plurality of cells within the embryo following the initial transduction event. If the avian cell is derived from an embryonated chicken egg, for example if the cell is a CEF, passaging the cell may involve maintaining the cells and facilitating division of the cell using standard cell culture techniques, such as the regular splitting of the cells into new tissue culture vessels to maintain the required culture density.

Vaccines may comprise dead/inactivated viruses or purified products thereof. Alternatively, vaccines may comprise live, attenuated viruses that have been cultivated under conditions that lead to a loss of virulence whilst retaining immunogenicity. For example, the disease-causing virus may be passaged through a series of cell cultures or animal embryos until a point at which it is sufficiently poor at replicating in its target cells that it can be used as a vaccine. At this point the virus has lost virulence but is still immunogenic and able to stimulate an immune response. Attenuated viruses for use in vaccines are commonly produced by passaging the virus in embryonated chicken eggs and/or cells derived from embryonated chicken eggs, such as GEFs, to such a point where the virus is no longer virulent for its original host cell and therefore no longer virulent for its original host species.

The ability of IFITM polypeptides to restrict infection by viruses which do not commonly target the host cell in which they are being expressed is important in the context of the generation of attenuated viruses for use in vaccines. The reduction of IFITM expression and/or activity in an avian host cell may increase the susceptibility of the host cell to infection by non-avian viruses, for example mammalian, such as human, viruses.

The present invention therefore provides a method for generating an attenuated virus comprising the following steps:

(i) transducing an avian cell according to the first aspect with a virus; and, (ii) passaging the avian cell such that the virus completes multiple rounds of infection and becomes attenuated.

The methods of propagating and/or attenuating viruses provided by the present invention involve reducing the protein level of IFITM1, IFITM2 and/or IFITM3, or a homologue thereof in avian embryos or avian cells that are used to passage viruses, IFITM proteins function to inhibit viral infection and therefore cells in which the level of IFITM. expression or activity is diminished are more susceptible to viral infection. The increased susceptibility of the cells to viral infection results in a higher efficiency of viral infection, with more cells being infected and more virus produced in comparison to cells in which the level of IFITM expression is not manipulated. Such characteristics are beneficial for improving the yield of virus production in applications that involve passaging viruses in host cells.

The first aspect of the present invention relates to an avian cell having reduced expression and/or activity of Chicken IFITM1 (SEQ ID No. 1); Chicken IFITM2 (SEQ ID No. 2) and/or Chicken IFITM3 (SEQ ID No. 3) or their homologous sequence(s).

The term “reduced” indicated that the expression or activity of the IFITM is less than the expression or activity of the IFITM in an equivalent unmodified or untreated, wild-type cell.

The expression or activity of the IFITM may be reduced by, for example, up to 25, 50 or 75%.

Avian embryos or avian cell lines with reduced IFITM expression or activity may be generated by a number of techniques known, to the person skilled in the art.

IFITM gene expression may be reduced via the RNA interference (RNAi) pathway using RNAi mediators such as antisense RNA, short-interfering RNA (siRNA), microRNA or short-hairpin RNA (shRNA). RNAi-mediator molecules may be delivered transiently as naked RNA, in plasmid vectors, or in lipid and/of protein capsules via techniques such as electroporation, lipofection or nanoparticle delivery. Alternatively RNAi-mediator molecules may be stably introduced into the genome of target cells through the use of retrovirus vectors, for example lentivirus, wherein target cells are transduced with lentivirus such that the lentiviral genome integrates into the genome of the target cell. If lentivirus vectors which comprise a tractable marker such as GFP are used, the cells in which the RNAi-mediator molecule is expressed can be selected. Because the lentivirus genome is stably integrated into the host cell genome inherited expression of the RNAi-mediator molecule is permitted and hence stable progeny expression reduced levels of IFITM are generated.

Confirmation of reduced IFITM expression can be assessed using a number of techniques that are well known in the art. For example the level of IFITM mRNA can be assessed using conventional or real-time PCR techniques and IFITM protein levels can be assessed by western blotting techniques.

A transgenic animal in which the expression of one or more of the following polypeptides, or a homologue thereof: Chicken IFITM1 (SEQ ID No. 1); Chicken IFITM2 (SEQ ID No. 2) and Chicken IFITM3 (SEQ ID No. 3) is reduced or knocked-out in the germ cells and somatic cells of said animal may be produced by lentiviral delivery of an RNAi-mediator molecule targeted against one or more nucleotide sequence encoding for said polypeptide to mature oocytes, spermatozoa, newly fertilized zygotes, early embryos or Primordial Germ Cells (PGC) of said animal at the appropriate developmental stage. This will result in the expression of the RNAi-mediator molecule in the progeny of the cell and diminished expression of the polypeptide encoded by the targeted gene.

The activity of one of the above polypeptides may be reduced by the delivery of a transgenic sequence encoding a dominant-negative mutant version of the polypeptide to the mature oocytes, spermatozoa, newly fertilized zygotes, early embryos or Primordial Germ Cells (PGC) of said animal at the appropriate developmental stage.

Alternatively knock-outs of target genes may be generated by homologous or targeted recombination events.

IFITM encoding genes may also be replaced with nucleotide sequences that do not encode for a functional IFITM protein using the above described techniques. In the contest of the present invention, the term “functional” refers to the ability of the IFITM polypeptide to inhibit viral infection of a host cell when expressed in that cell.

Vaccine

Viruses propagated and/or attenuated by methods of the present invention may be incorporated into vaccines.

The term 'vaccine' as used herein refers to a preparation which, when administered to a subject, induces or stimulates a protective immune response. A vaccine can render an organism immune to a particular disease.

The vaccine may be used therapeutically, to treat an existing infection; or prophylactically, to block or reduce the likelihood of infection and/or prevent or reduce the likelihood of contracting the disease.

A vaccine comprises one or more vaccinating entity(ies) and optionally one or more adjuvants, excipients, carriers and diluents.

The vaccinating entity may be a virus propagated and/or attenuated by a method of the present invention.

The vaccinating entity may also be a purified product of the virus propagated and/or attenuated by a method of the present invention.

The vaccine may also comprise, or be capable of expressing, another active agent, for example one which may stimulate early protection prior to the vaccinating entity-induced adaptive immune response. The agent may be an antiviral agent, such as type I interferon. Alternatively, or in addition, the agent may be granulocyte-macrophage colony-stimulating factor (GM-CSF).

Investigating the Innate Resistance of an Avian Animal to Viral Infection

The present invention provides a method far investigating the innate resistance of an avian animal to viral infection which comprises the step of investigating the nucleotide sequence encoding for one or more of the following polypeptides, or a homologue thereof: Chicken IFITM1 (SEQ ID No. 1); Chicken IFITM2 (SEQ ID No. 2) and Chicken IFITM3 (SEQ ID No. 3) and/or the copy number thereof.

Investigating the sequence of a nucleotide sequence encoding an IFITM polypeptide, for example an IFITM gene, may be performed by screening IFITM genes for sequence variation. The screening of IFITM variants may be performed using a number of conventional techniques which are well known in the art and include, but are not limited to, PCR, conventional DNA sequencing and second-generation DNA sequencing.

The copy number of a gene is the number of copies of five gene which occur in the genome. Copy-number variations (CNVs) are alterations of the DNA of a genome that results is the cell having an abnormal number of copies of one or more genes. CNVs usually arise when relatively large regions of the genome have been deleted (giving fewer than the normal number of copies of a gene) or duplicated (giving more then the normal number of copies of a gene) on certain chromosomes.

Copy number variation can be investigated by cytogenetic techniques such as fluoroescent in situ hybridization, comparative genomic hybridization, array comparative genomic hybridization, virtual karyotyping with SNP arrays and next-generation sequencing.

In addition to the method for screening IFITM genes described above, the present invention also provides a method for selecting an avian animal having resistance to viral infection from a plurality of avian animals of the same species. Such a method comprises the steps of investigating the sequence and/or copy number of one or more avian IFITM genes as described above and selecting and avian animal having an IFITM1, IFITM2 and/or IFITM3 sequence or copy number which is associated with resistance to viral infection.

The plurality of animals that are screened and potentially selected from in the above methods may comprise a flock, a breed or a species. Due to the possible variation in the genetic sequence of IFITM genes, different animals within a population may be associated with different IFITM sequences. Such differences in the genetic sequence of an IFITM gene between individual members of a population may be referred to as the genetic variation within the plurality.

Inhibiting Viral Infection

The term "to inhibit viral infection" refers to the ability of a polypeptide to decrease, inhibit or reduce the level of virus entry into, replication within or release from a cell. An avian animal expressing a polypeptide that is able to inhibit viral infection is therefore associated with resistance to viral infection.

A number of techniques for assessing levels of viral infectivity are known in the art. These techniques typically involve determining the presence of viral replication markers, for example assaying levels of viral RNA, viral peptides and/or virus particles or assaying the level of mortality, in a population that has been infected with a virus. Such techniques are commonly used to determine the potential anti-viral function of an entity such as a polypeptide, or nucleotide sequence, by increasing or decreasing the level of a candidate anti-viral entity in a sample and comparing the level of viral infectivity to an equivalent sample in which the level of the anti-viral entity has not been modulated. Techniques for assessing levels of viral infectivity include, but are not limited to, plaque assays, flow cytometry, qPCR, ELISA and mortality rates.

Viral Infections

The polypeptide of the present invention is able to inhibit viral infection.

The viral infection may be caused be any virus that enters the target cell through acidic endosomes. Such entry involves the uptake of the virus into the target cell via endocytosis prior to processing through the endosomal pathway. As the endosome is processed and matures in the cell its pH becomes more acidic and the increasing acidity results in changes to the conformation of the endosome which allows the virus to be liberated into the cell.

The viral infection may be caused by an avian and/or a mammalian virus. The virus may be an enveloped virus. IFITMs block cytosolic entry of enveloped viruses by blocking virus envelope fusion with cell endosomal membranes.

The avian viral infection may be avian influenza, avian infectious bronchitis, infectious bursal disease, Marek's disease or Newcastle Disease.

Avian influenza is caused by the Avian Influenza Virus (AIV), which is an influenza A virus of the Orthomyxoviridae family. All subtypes (but not all strains of all subtypes) of influenza A virus are adapted to birds and strains of all subtypes of influenza A virus have been isolated from wild birds, wherein they are often carried without the presentation of disease symptoms. Some isolates of influenza A virus, however, may cause severe disease both in domestic poultry and occasionally, in humans. Influenza A viruses are negative-sense, single-stranded, segmented RNA viruses. They are defined according to an H number, for the type of hemagglutinin, and an N number, for the type of neuraminidase, that is present on the virus capsid. There are 17 different H antigens (H1 to H17) and nine different N antigens (N1 to N9). Subtypes of AIV include, but are not limited to N1N1, H5N1, H5N2, H5N8, H7N1, H7N3 and H7N7.

AIV cell entry and replication is a multi-step process which involves virus entry into host cells via interactions between viral hemagglutinin and host sialic acid, release of live virus RNA genome (vRNA) and viral core proteins within the context of acidic endosomal compartments, conversion of vRNA to mRNA to facilitate expression of viral proteins, replication of vRNA and release of viral particles from infected cells via blebbing.

Symptoms in birds are variable and can be unspecific but may include ruffled feathers, reduction in egg production and weight loss combined with respiratory disease. In its most highly pathogenic form, AIV in chickens and turkeys produces a sudden appearance of severe symptoms and almost 100% mortality within two days. These outbreaks can cause large economic losses to poultry farmers.

Avian infectious bronchitis is caused by the avian Infectious Bronchitis Virus (IBV). IBV is a highly infectious coronavirus that infects avian species, including chickens, and affects the respiratory tract, gut, kidney and reproductive systems.

IBV has a non-segmented, positive-sense single stranded RNA genome and replicates via entry into host cells in acidic endosomes followed by release of viral genomic RNA into the cytoplasm. The Coronavirus genome has a 5' methylated cap and a 3'polyadenylated tail which allows the RNA to attach to ribosomes for direct translation. Coronaviruses also encode a replicase, which allows the RNA viral genome to be transcribed into new RNA copies using the host cells machinery.

Infectious bursal disease (also known as IBD, Gumboro Disease, Infectious Bursitis or Infectious Avian Nephrosis) is a highly contagious disease of young chickens caused by the Infectious Bursal Disease Virus (IBDV). IBDV is a double stranded RNA virus that has a bi-segmented genome and belongs to the genus *Avibirnavirus* of the family Birnaviridae. IBDV enters host target cells via acidic endosomes. There are two distinct serotypes of the virus, but only serotype 1 viruses cause disease in poultry. At least six antigenic subtypes of IBDV serotype 1 have been identified and variants within this subtype are able to break through high levels of maternal antibodies in commercial flocks, causing up to 60 to 100 percent mortality rates in chickens.

IBD is characterized by immunosuppression and mortality, generally at 3 to 6 weeks of age. Disease symptoms may appear suddenly and morbidity typically reaches 100%. Infected birds may produce a watery diarrhoea and may have swollen feces-stained vent. The majority of the infected flock may be recumbent and have ruffled feathers. The infection primary affects the bursa of Fabricius and results in infected birds being immunocompromised.

Marek's disease is a highly contagious viral neoplastic disease of chickens caused by an alphaherpesvirus known as Marek's Disease Virus serotype 1 (MDV-1) or Gallid herpesvirus 2 (GaHV-2). The disease is characterized by the presence of T cell lymphoma and the infiltration of nerves and organs by lymphocytes. The six syndromes known to occur after MDV-1 infection are; neurolymphomatosis, acute Marek's disease, ocular lymphomatosis, cutaneous Marek's disease, atherosclerosis and immunosuppression.

MDV-1 comprises a DNA genome and is nuclear-replicating, with the viral DNA being transcribed to mRNA within the infected cell's nucleus, infection is initiated when viral envelope glycoproteins interact with target cell membrane receptors causing the virion to be internalized within acidic endosomes and dismantled, allowing viral DNA to migrate to the cell nucleus. Once within the nucleus, replication of viral DNA and transcription of viral genes occurs.

During symptomatic infection, infected cells transcribe lytic viral genes that lead to the death of infected host cells. In addition to lytic viral genes, host cells can also express latency associated transcripts (LAT) instead. In this fashion the virus can persist in the cell (and thus the host) indefinitely.

Newcastle Disease is caused by the avian paramyxovirus, Newcastle Disease Virus (NDV). The genomes of paramyxoviruses are non-segmented negative-sense RNA, 15-19 kilobases in length. Signs of infection with NDV vary greatly depending on factors such as the strain of virus and the health, age and species of the host but include: respiratory signs (gasping, coughing), nervous signs (depression, inappetence, muscular tremors, drooping wings, twisting of head and neck, circling, complete paralysis), swelling of the tissues around the eyes and neck, greenish, watery diarrhoea, misshapen, rough- or thin-shelled eggs and reduced egg production. In acute cases, death may be sudden, and, in the beginning of the outbreak, the remaining birds may not be symptomatic. In flocks with good immunity, however, the signs (respiratory and digestive) are mild and progressive, and are followed after seven days by nervous symptoms, especially twisted heads. NDV strains can be categorised as velogenic (highly virulent), mesogenic (intermediate virulence) or lentogenic (nonvirulent). Velogenic strains produce severe nervous and respiratory signs, spread rapidly and cause up to 90% mortality. Mesogenic strains cause coughing, affect egg quality and production and result in up to 10% mortality. Lentogenic strains produce mild signs with negligible mortality.

The polypeptide of the present invention may be used in the prevention or treatment of viral disease.

The use of the polypeptide for the prevention of viral disease relates to its use as a prophylactic entity. Herein the polypeptide, or a nucleic acid encoding the polypeptide, may be administered to an avian animal who has not yet contrasted the disease and/or who is not showing any symptoms of the disease to prevent or impair the cause of the disease or to reduce or prevent development of at least one symptom associated with the disease.

The use of the polypeptide for the treatment of viral disease relates to its use as a therapeutic entity. Herein the polypeptide, or a nucleic acid encoding the polypeptide, may be administered to an avian animal having an existing disease or condition in order to lessen, reduce or improve at least one symptom associated with the disease and/or to slow down, reduce or block the progression of the disease.

Increasing Expression

The present invention provides a method for preventing or treating a viral infection in an avian animal which comprises the step of increasing the expression of one or more of the following polypeptides, or a homologue thereof: Chicken IFITM1 (SEQ ID No. 1); Chicken IFITM2 (SEQ ID No. 2) and Chicken IFITM3 (SEQ ID No. 3) in the animal.

Expression may be increased by, for example, transfecting or transducing the avian animal with the relevant gene(s). The gene(s) may be introduced by a vector-based method. The vector may be a viral or non-viral vector.

The vector may be used in a "gene-therapy" type approach to cause a permanent increase the copy number of the gene(s) on the genome of the avian animal.

Expression may also be increased by modulating the promoter and/or enhancer(s) which control the expression of the gene(s).

Transgenic Avian Animals

As stated above, sequence variants of IFITM polypeptides may vary in their ability to inhibit viral infections. In addition, increased levels of IFITM expression may correlate with increased protection against viral infection. As such the present invention also relates to a method for producing an avian animal having increased resistance to viral infection, the method comprising increasing the expression of one, two or three of avian IFITM1, 2 and 3 in the avian animal or inducing the expression or over-expression of an active variant(s) thereof or increasing the copy number thereof on the genome.

The transgenic avian animal may be a transgenic chicken.

As used herein, the terms exogenic, transgenic, and heterogenic are all synonymous for nucleic acid sequences intentionally introduced into the genome of a subject by human intervention rather than by spontaneous mutation. All methods of producing transgenic animals, including transgenic chickens, rely on techniques designed to inset novel genetic material into cells that will give rise to germ cells. As such mature oocytes, spermatozoa, newly fertilized zygotes, early embryos or Primordial Germ Cells (PGC) may be used as the target for introducing the transgene.

Methods that may be used for generating transgenic animals am well known in the art and include, but are not limited to, virus-mediated gene transfer, DNA microinjection, embryonic stem/primordial cell mediated gene transfer, nuclear transfer, artificial chromosome transfer, testis mediated gene transfer and sperm mediated gene transfer.

The present invention also provides a transgenic avian animal whose germ cells and somatic cells comprise a heterogenic nucleotide sequence, which encodes for a polypeptide of the present invention, introduced into said animal, or an ancestor of said animal, at an embryonic stage.

The invention will now be further described by way of Examples, which are meant to serve to assist one of ordinary skill in the art in carrying out the invention and are not intended in any way to limit the scope of the invention.

EXAMPLES

Example 1—Mining Chicken IFITM Sequences

TBLASTN analysis of the most recent version of the chicken genome (v4.0, NCBI browser) revealed three chicken IFITMs. Two of these had previously been identified and designated IFITM3-like (NCBI I.D. XM_420925.3) and IFITM1-like (variant 1: XM_001233949.2; variant 2: XM_003641281.1). All of the chIFITM paralogues, like mammalian IFITMs, are comprised of two exons and the location of the intron-exon boundary is conserved across all of these species.

Example 2—Annotating the Chicken IFITM Genes

Figure 1:
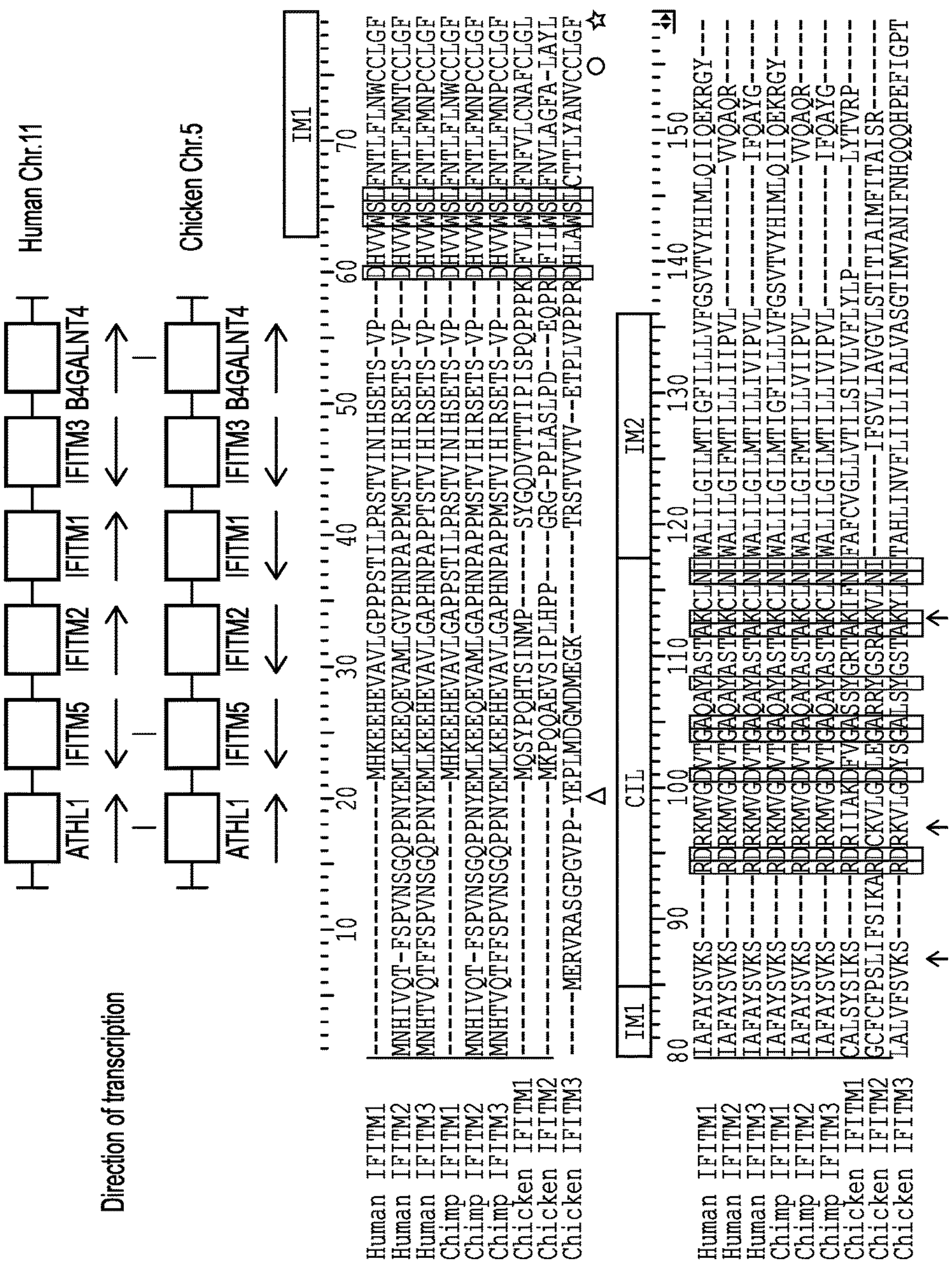
FIG. 1: The chIFITM locus architecture and multiple sequence alignments

Amino acid alignments between the 3 chIFITM genes and direct orthologues in primate species show a number of conserved IFITM-family motifs are present in some of the chicken sequences (FIG. 1B). The chicken sequences differ significantly from the human and chimp orthologues; however a number of residues, most of which lie in the conserved intracellular loop (CIL) domain, are conserved. Multiple sequence alignments also reveal some important residues in the chicken IFITM genes that help to categorise each sequence as either IFITM1 or IFITM2/3. Tyr20 is conserved in all primate IFITM2 or 3 sequences, and is also present in chicken IFITM3 but not in any of the other IFITM1 orthologues. The alignment also reveals other functionally important residues are conserved in some of the chicken IFITM sequences, including the two cysteines (Cys75-76) in intramembrane 1 (IM1) which have been shown to be palmityolated in other species and are important for membrane positioning, Phe79, also in IM1, is conserved in chicken IFITM3. Analysis of the conserved synteny between the human IFITM locus and this region of the chicken genome (v4.0, NCBI) alongside an exhaustive analysis of key residues, has resulted in the defining of the chIFITM genes as chicken IFITM3 (chIFITM3) (previously "NCBI chicken IFITM1-like") and chicken IFITM1 (chIFITM1) (previously "NCBI chicken IFITM3-like"). A novel chIFITM, chIFITM2, has also been identified (FIG. 1).

Example 3—Infecting IFITM Expressing Cell Lines with Pseudotyped Viruses

There was a negative correlation between the level of chIFITM3 being overexpressed and the percentage of cells infected by a lentivirus vector pseudotyped with the lyssavirus envelopes LBV (FIG. 6).

The level of antiviral restriction of the chicken IFITMs was compared to their orthologous human proteins in A549 cells. Over-expression of chIFITM3 resulted in 94-98.5% reduction in infection of A549 cells to a range of lentivirus vectors pseudotyped with the lyssaviruses envelopes; RABV, LBV and MOKV. This was very similar to the level of restriction by huIFITM3 to the same viruses (FIG. 2) even though chickens are rarely infected by lyssaviruses. ChIFITM2 also restricts lyssavirus LBV and RABV infection by 70%, however it only minimally restricts MOKV lyssavirus (20%). A similar pattern of restriction is seen for lentiviruses pseudotyped with IAV H1, H4, H5, H7 and H10, HuIFITM3 and chIFITM3 restrict viral Infection of all influenza haemagglutinins very effectively, reducing infection by greater than 90%. ChIFITM2 and huIFITM2 restrict more moderately, although chIFITM2, which had limited activity against the MOKV lyssavirus envelope, restricted influenza H4 to a similar level as chIFITM3. Similarly huIFITM2 showed greater restriction of influenza H1 and H4 than to H5. Overall, although chIFITM3 and huIFITM3 only share 42% amino acid identity, the level of viral restriction of chIFITM3 is equivalent to huIFITM3, in contrast to huIFITM3 and huIFITM2, which share 90% sequence identity but show different patterns of virus restriction.

Example 4—Cellular Localisation of IFITM Proteins

The cellular localisation of IFITM proteins in the transduced A549s was established by fluorescence microscopy using an anti-HA antibody directly conjugated to FITC. Chicken IFITM3 and huIFITM3 localise peri-nuclearly whereas chIFITM1 and huIFITM1 localise throughout the cytoplasm (FIG. 3).

Example 5—Constitutive Expression Knock-Down in DF-1 Chicken Cells

The basal level of chIFITM3, measured by quantitative RT-PCR, In DF-1 cells is relatively high, but addition of IFN-γ resulted in a moderate induction (FIG. 4A). Prior treatment with an siRNA targeting chIFITM3 in IFN-γ treated cells resulted in a 1.47 log fold drop in expression. This log fold reduction is equivalent to a 62.9% known-down in relative expression (FIG. 4B).

To further investigate the function of chIFITM3 in native chicken cells, its expression during influenza infection was investigated. The percentage of DF-1 cells infected by influenza (A/WSN/1933) increased from 14.0% after no siRNA treatment, to 31.5% infection when pre-treated with an siRNA targeting ChIFITM3 (FIG. 4C).

The inventors assessed the constitutive level of expression of chIFITM3 in DF-1 cells, by quantitative RT-PCR with primers for chIFITM3. DF-1 cells abundantly express chIFITM3 (threshold cycles [CTs] of 20 for IFITM3 and 22 for GAPDH). Despite being IFN inducible, addition of IFN-γ resulted in only a moderate induction, whereas addition of IFN-α caused a 2.67-log 2 (6.4-fold) increase in chIFITM3 expression (FIG. 7A).

chIFITM3 expression in DF-1 cells was knocked down using an siRNA designed to the chIFITM3 transcript. Treatment with this siRNA on unstimulated DF-1 cells resulted in a 1.23-log 2 (2.4-fold) induction in the transcript level, with no change in chIFITM3 transcript abundance with a non-specific siRNA. Knockdown of endogenous chIFITM3 resulted in a greater than 2-fold increase in infection of DF-1 cells by replication-competent influenza A virus (A/WSN/1933) (FIG. 5B), assayed by flow cytometric analysis of NP expression.

Furthermore, overexpression of chIFITM3 in DF-1 cells reduced viral replication by an average of 55% (FIG. 7D), and plaque assays show that the viral bad was reduced from 1.3×106 FPU ml-l to 3.1×105 PFU ml-l after chIFITM3 overexpression (FIG. 7E). Together, these results show chIFITM3 is able to restrict IAV entry into DF-1 cells.

Example 6—chIFITM Expression in an RNA Tissue Panel

Primers specific to chIFITM1, 2 or 3 were used to amplify mRNA transcripts using RT-PCR in a range of tissue types. Expression of IFITM2 and 3 was constitutively expressed in all cell lines tested (FIG. 5), but expression of IFITM1 was confined to the bursa (an organ needed for B-cell development), the gastro-intestinal tract, the caecal tonsil and the trachea.

MATERIALS AND METHODS

Plasmids.

All IFITM genes were cloned into the BamHI and NotI sites of pSIN-BNHA and sequences confirmed by capillary sequencing (GATC biotech).

Cell Culture Conditions.

A549 cells were grown in F-12 (Invitrogen) and HEK293T and DF-1 cells were grown in DMEM (Invitrogen), all media was supplemented with 1.0% v/v FBS (Biosera).

Generating IFITM Expressing Cell Lines.

Chicken and human IFITM gene sequences were ordered from GeneArt (Life Technologies) and were codon optimised for expression in human cells. The gene cassette was inserted into a lentiviral plasmid, pSIN-BNHA, which would ensure that a C-terminal HA tag followed the IFITM protein. Lentivirus was made by a 3 plasmid transfection of HEK293-T cells, grown to confluence in a 10 cm dish. OptiMEM (200 μl Gibco) was mixed with 10 μl of Fugene-6 (Roche). The DNA for transfection was made up in a final volume of 15 μl Tris-EDTA (TE), containing 1 μg of a gag-pol expressing vector (p8.91), 1 μg of a VSV-G expressing vector (pMDG) and 1.5 μg of vector expressing the transgene (pSIN-BNHA). The DNA was added to the OptiMEM solution and incubated for 15 minutes (min). Once the media was removed from the cells and replaced with 8 ml of DMEM, 10% FBS, the DNA mixture was added dropwise to the cells. After 24 hours (h) at 37° C. and 5% $CO_2$ the media was removed and replaced with 8 ml DMEM, 10% FBS, and incubated for a further 24 h. Packaged virus was harvested at 48 and 72 h after transfection by collecting the supernatant and filtering using a 0.45 μM filter (Millex). Aliquots (1 ml) were frozen down at −80° C. The lentiviruses were used to transduce human A549 lung epithelial cells and produce a mixed population.

Confocal Microscopy.

Cells were seeded at 1 . . . 105/well on coverslips in a 12-well plate 1 day prior to transaction with an IFITM-encoding plasmid (1 μg DNA with 3 μl of Fugene [Promega]). Cells were fixed with 100% methanol for 10 min followed by being blocked in 1% bovine serum albumin (BSA) for 30 min. The HA epitope was targeted by an anti-HA antibody conjugated to Alexa Fluor S50 (ab117513), and endosomes were visualized by a Lamp1 antibody with human (ab25630; Abcam) or chicken (LEP100 IgG; Development Studies Hybridoma Bank) specificity, followed by incubation with a secondary antibody conjugated to Alexa Fluor 488 (ab96871; Abcam).

Single Cell Cloning.

All wells of a clean, flat-bottomed 96 well plate (Corning) were filled with 100 μl of culture media, except well A1, 200 μl of cell suspension ($2\times10^4$ cells/ml) was added to well A1, followed by a 1:2 serial dilution out to well H1. An additional 100 μl of culture media was added to all wells in column 1 and another serial dilution was carried out along each row of the plate to column 12. A further 100 μl of media was added to all wells in the 96 well plate to bring the final volume of each well to 200 μl before incubating the plate at 37° C. for 4-5 days. Wells whip only 1 clone in them were marked and allowed to expand, before harvesting into a 24 well plate and allowed to reach confluence. Cells were prepared for flow cytometric analysis, and colonies with a high level of HA expression were transferred to T25 flasks.

Flow Cytometric Analysis.

Media from each well was collected in a 2 ml Eppendorf tube. The cells were detached from the plastic using 300 μl 0.25% Trypsin-EDTA (Invitrogen), neutralised with 300 μl of cell culture media, 10% FBS and pooled with the supernatant. The cells were spun at 2000 g for 5 min, the pellet resuspended in 100 μl PBS and transferred to 96 well v-bottomed plate (Nunc). The plate was centrifuged again and the cells fixed and permeablised in 100 μl of Cytofix/Cytoperm™ buffer (Becton Dickinson) and washed according to manufacturer's guidelines. The cells were resuspended in the primary antibody (Table S4) and incubated for 1 h at 4° C., followed by two rounds of washing. Cells were subsequently resuspended in the secondary antibody conjugated to a fluorescent protein and incubated in the dark for 1 h, unless the primary antibody had a conjugated fluorescent marker. Cells were washed again, resuspended in 300 μl of PBS before analysis by flow cytometry (FACSCalibur II, Becton Dickinson). Cells that expressed GFP were fixed with 4% v/v paraformaldehyde (USB) for 20 min, washed twice with PBS and resuspended in 300 μl of PBS prior to analysis by flow cytometry.

Infecting IFITM Expressing Cell Lines with Pseudotyped Viruses.

Chicken or human IFITM expressing A549 cell lines were seeded at $3\times10^3$ cells/well in 96 well plates, one day prior to infection with either GFP expressing pseudotyped lyssaviruses (RABV Challenge virus standard-11 (CVS-11;

EU352767), Lagos bat virus (LBV.NIG56-RV1; HM623779) and mokola virus (MOKV.98/071 RA361; GQ500108) or luciferase expressing pseudotyped influenza viruses (HA1 (AF117241), HA4 (D90302), HA5 (EF541394), H7 (AJ49I720), and H10 (CYD01467I)). GFP expression, as a measure of lentivirus infection, was measured by fluorescence microscopy at 48 h post infection following fixation with 4% v/v paraformaldehyde (USB) for 20 min. Cells were washed with 100 μl of PBS/Hoechst solution (Life Technologies, 200 ng/μl) and a plate seal adhered. The cells were analysed to determine the proportion of cells expressing GFP (Cellomics ArrayScan VTI, Thermofisher), according to the manufacturer's instructions. Luciferase activity, as a measure of lentivirus infection, was determined at 48 h post exposure using the 50 μl Bright-Glo™ reagent (Promega). The cells were allowed to lyse for 2 min before the level of luciferase activity was measured using the FLUOstar omega (BMC Labtech). GFP and luciferase levels are reported relative to infection of A549 cells in the absence of IFITM protein over-expression. The percentage of cells infected that express IFITM proteins is recorded as a proportion of the infection in untransduced A549 cells (normalised to 100%).

Cellomics Fluorescent Cell Analysis.

Cells were seeded sparsely ($3\times10^3$/well of a clear flat-bottomed 96 well plate, Corning) and infected with a GFP expressing virus. 48 h later cells were washed in 100 μl of PBS and fixed with 4% v/v paraformaldehyde (USB) for 20 min. Cells were washed with 100 μl of PBS/Hoechst solution (Invitrogen, 200 ng/μl) and a plate seal adhered. The cells were analysed to determine the proportion of cells expressing GFP (Cellomics ArrayScan VTI, Thermofisher), according to the manufacturer's instructions.

Luciferase Reporter Assays.

Cells were seeded at $3\times10^3$/well in white flat-bottomed 96 well plates (NUNC) and left for 24 h at 37° C. An appropriate volume of pseudotyped virus expressing the protein coat of an influenza virus and a luciferase reporter gene was added to the cells and incubated for 48 h at 37° C. The cells were removed from the incubator to reach room temperature before 50 μl Bright-Glo™ reagent (Promega) was added to each well. The cells were allowed to lyse for 2 min before the level of luciferase activity was measured using the FLUOstar omega (BMG labtech).

siRNA Knock-Down Studies.

DF-1 cells were seeded at $5\times10^4$/well in a 24 well plate. Cells were exposed to siRNAs again chIFITM3 (gcgaagtacctgaacatcacg) or a non-specific siRNA (uucuccgaacgugucacgugu) diluted in Lipofectamine RNAiMax (Invitrogen), for 48 h. The cells were stimulated by addition of either 200 ng/ml of chicken IFN-γ (Kingfisher biotech #RP0115c) for a further 24 h or influenza A virus (A/WSN/1933 (WSN/33)) for 1 h at an MOI of 0.1. RNA was extracted (RNAeasy minikit, Qiagen) according to the manufacturer's instructions. RT-PCR was carried out (QuantiTect Multiplex RT-PCR kit, Qiagen) using probes and primers from ABI (chicken GADPH; 4448489 and chicken_IFITM3; custom assay) see Table S1. Influenza infection was measured by flow cytometric analysis (see above) using an anti-NP antibody (ab20921, AbCam).

Plaque Assays.

Material to be assayed was serially dilated in serum free DMEM and used to infect MDCK cells in 12-well plates. After 1 h of incubation, the inoculum was removed, and the cells were overlaid with DMEM containing 0.2% BSA (Sigma-Aldrich), 1.25% Avicel (FMC Biopolymer), and 1 μg trypsin $ml^{-1}$. After 2 days, the overlay was removed, and the cells were fixed with 4% formal saline-PBS solution for 20 min before being stained with 0.1% toluidine blue solution (Sigma-Aldrich) so that the number of PFU could be calculated.

Expression of IFITM Proteins in Different Chicken Tissues.

Tissues were removed from 6-to 9-wk-old specific pathogen-free (SPF) Rhode Island red (RIR) chickens, specifically thymus, spleen, bursa of Fabricius, Harderiangland, caecal tonsil, Meckel's diverticulum, bone marrow, brain, muscle, heart, liver, kidney, lung, and skin. RNA was DNase treated and reverse transcription was carried out (SuperScript III reverse transcriptase, Invitrogen). The cDNA from each tissue was amplified by PCR using the following primer sets: chIFITM1 (F'-AGCACACCAGCATCAACATGC (SEQ ID NO: 8), R'-CTACGAAGTCCTTGGCGATGA (SEQ ID NO: 9)), chIFITM2 (F'-AGGTGAGCATCCCGCTGCAC (SEQ ID NO: 10), R'-ACCGCCGAGCACCTTCCAGG (SEQ ID NO:11)) and chIFITM3 (F'-GGAGTCCCACCGTATGAAC (SEQ ID NO: 12), R'-GGCGTCTCCACCGTCACCA (SEQ ID NO: 13)). Primers amplifying GAPDH (F'-ACTGTCAAGGCTGAGAACGG (SEQ ID NO: 14), R'-GCTGAGGGAGCTGAGATGA (SEQ ID NO: 15)) were designed to span an intron-exon border, which allowed detection of and differentiation between cDNA and gDNA amplification, and was used as a loading control.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in virology, molecular biology or related fields are intended to be within the scope of the following claims.

The invention claimed is:

1. An isolated chicken cell or a chicken cell within an embryonated egg comprising:

i) an endogenous interferon-inducible transmembrane protein 2 (IFITM2) gene encoding an IFITM2 protein with at least 95% sequence identity to the amino acid sequence of SEQ ID NO: 2; and ii) an interfering RNA that targets the IFITM2 gene, wherein the isolated chicken cell or chicken cell within an embryonated egg has reduced expression of the IFITM2 gene and increased susceptibility to viral infection as compared to an isolated chicken cell or a chicken cell within an embryonated egg comprising the endogenous IFITM2 gene that does not comprise the interfering RNA.

2. A method for propagating a virus, comprising:

i) transducing the isolated chicken cell or the chicken cell within an embryonated egg of claim 1 with a virus: and ii) passaging the cell such that the virus is propagated.

3. A method for producing a vaccine comprising: (i) propagating a virus according to the method of claim 2; and (ii) incorporating the propagated virus into a vaccine.

4. A method for generating an attenuated virus, comprising:

i) transducing the isolated chicken cell or the chicken cell within an embryonated egg of claim 1 with a virus: and ii) passaging the cell such that the virus completes multiple rounds of infection and becomes attenuated.

5. A method for producing a vaccine comprising: i) generating an attenuated virus according to the method of claim 4; ii) propagating the attenuated virus; and iii) incorporating the virus propagated in step ii) into a vaccine.

6. The isolated chicken cell or chicken cell within an embryonated egg of claim 1, further comprising:

i) an endogenous interferon-inducible transmembrane protein 1 (IFITM1) gene encoding an IFITM1 protein with at least 95% sequence identity to the amino acid sequence of SEQ ID NO: 1; and ii) an interfering RNA that targets the IFITM1 gene, wherein the isolated chicken cell or chicken cell within an embryonated egg has reduced expression of the IFITM1 gene as compared to an isolated chicken cell or a chicken cell within an embryonated egg comprising the endogenous IFITM1 gene that does not comprise the interfering RNA that targets IFITM1.

7. The isolated chicken cell or chicken cell within an embryonated egg of claim 1, further comprising:

i) an endogenous interferon-inducible transmembrane protein 3 (IFITM3) gene encoding an IFITM 3 protein with at least 95% sequence identity to the amino acid sequence of SEQ ID NO: 3; and ii) an interfering RNA that targets the IFITM3 gene, wherein the isolated chicken cell or chicken cell within an embryonated egg has reduced expression of the IFITM3 gene as compared to an isolated chicken cell or a chicken cell within an embryonated egg comprising the endogenous IFITM3 gene that does not comprise the interfering RNA that targets IFITM3.

8. The isolated chicken cell or chicken cell within an embryonated egg of claim 1 comprising an endogenous interferon-inducible transmembrane protein 2 (IFITM2) gene encoding an IFITM2 protein with 100% sequence identity to the amino acid sequence of SEQ ID NO: 2.

* * * * *

UNITED STATES PATENT AND TRADEMARK OFFICE

CERTIFICATE OF CORRECTION

PATENT NO. : 10,202,578 B2
APPLICATION NO. : 14/895866
DATED : February 12, 2019
INVENTOR(S) : Mark Fife et al.

It is certified that error appears in the above-identified patent and that said Letters Patent is hereby corrected as shown below:

In the Specification

At Column 7, Lines 1-6:
"SEQ ID NO: 3
MERVRASGPGVPPYEPLMDGMEGKTRSTVVTVETPLVPPPRDHLAWSLCT
TLYANVCCLGFLALVFSVKSRDRKVLGDYSGALSYGSTAKYLNITAHLIN
VFLIILIIALVASGTIMVANIFNHQQQHPEFIGPT"

Should read:
-- SEQ ID NO: 3
MERVRASGPGVPPYEPLMDGMDMEGKTRSTVVTVETPLVPPPRDHLAWSLCT
TLYANVCCLGFLALVFSVKSRDRKVLGDYSGALSYGSTAKYLNITAHLIN
VFLIILIIALVASGTIMVANIFNHQQQHPEFIGPT --.

In the Claims

At Column 36, Line 53, "virus: and" should be -- virus; and; --.

At Column 36, Line 61, "virus: and" should be -- virus; and --.

At Column 37, Line 17, "IFITM 3" should be -- IFITM3 --.

Signed and Sealed this
Twenty-second Day of December, 2020

Andrei Iancu
*Director of the United States Patent and Trademark Office*